US010005806B2

(12) United States Patent
Wu et al.

(10) Patent No.: US 10,005,806 B2
(45) Date of Patent: Jun. 26, 2018

(54) METALPORPHYRIN COMPLEX, PREPARATION METHOD THEREFOR AND METHOD FOR PREPARING POLYCARBONATE

(71) Applicant: CHANGCHUN INSTITUTE OF APPLIED CHEMISTRY, CHINESE ACADEMY OF SCIENCES, Jilin (CN)

(72) Inventors: Wei Wu, Jilin (CN); Yusheng Qin, Jilin (CN); Shuangbin Fu, Jilin (CN); Xianhong Wang, Jilin (CN); Fosong Wang, Jilin (CN)

(73) Assignee: Changchun Institute of Applied Chemistry, Chinese Academy of Sciences, Changchun, Jilin (CN)

( * ) Notice: Subject to any disclaimer, the term of this patent is extended or adjusted under 35 U.S.C. 154(b) by 46 days.

(21) Appl. No.: 14/915,880

(22) PCT Filed: Oct. 16, 2013

(86) PCT No.: PCT/CN2013/085276
§ 371 (c)(1),
(2) Date: Mar. 1, 2016

(87) PCT Pub. No.: WO2015/032113
PCT Pub. Date: Mar. 12, 2015

(65) Prior Publication Data
US 2016/0194346 A1    Jul. 7, 2016

(30) Foreign Application Priority Data
Sep. 5, 2013    (CN) .......................... 2013 1 0400892

(51) Int. Cl.
*C07D 487/22*    (2006.01)
*C08G 64/34*    (2006.01)
*C07F 15/02*    (2006.01)
*C07F 5/06*    (2006.01)
*C07F 15/00*    (2006.01)

(52) U.S. Cl.
CPC .......... *C07F 15/025* (2013.01); *C07D 487/22* (2013.01); *C07F 5/069* (2013.01); *C08G 64/34* (2013.01)

(58) Field of Classification Search
CPC .................................................. C07D 487/22
USPC .......................................... 528/412; 502/231
See application file for complete search history.

(56) References Cited

U.S. PATENT DOCUMENTS

2005/0038262 A1    2/2005    Lindset et al.

FOREIGN PATENT DOCUMENTS

CN    102558199 A    7/2012
CN    102731766 A    10/2012

OTHER PUBLICATIONS

International Search Report of PCT/CN2013/085276, dated Jun. 30, 2014, 3 pp.
Wu, et al., "New Bifunctional Catalyst Based on Cobalt-Porphyrin Complex for the Copolymerization of Propylene Oxide and $CO_2$", Journal of Polymer Science, Part A: Polymer Chemistry, No. 3, vol. 51, Nov. 15, 2012, pp. 493-498.
Liu, et al., "Preparation Method of 2, 4, 6-Trimethylbenzaldehyde", Chemistry and Adhesion, No. 6, vol. 31, Dec. 31, 2009, pp. 58-60 and 78.
Minkenberg, et al., "Responsive Vesicles from Dynamic Covalent Surfactants", Angew. Chem. Int. Ed., No. 15, vol. 50, Dec. 31, 2011, pp. 3421-3424.
Huang, et al., "A New Class of Conjugated Polymers Having Porphyrin, Poly(p-phenylenevinylene), and Fullerene Units for Efficient Electron Transfer", Macromolecules, No. 16, vol. 39, Dec. 31, 2006, pp. 5319-5325.
Qin, et al., "Copolymerization of Cyclohexene Oxide and Carbon Dioxide Catalyzed by Aluminum Porphyrin", Acta Polymerica Sinica, No. 7, Jul. 31, 2011, pp. 784-790.
Robic, et al., "Synthesis and Preliminary DNA-Interaction Studies of a new Cationic Porphyrin", Tetrahedron Letters, vol. 31, No. 33, 1990, pp. 4739-4742.
Roberts., et al., "Tunable Self-Assembly of Triazole-Linked Porphyrin-Polymer Conjugates", Chem. Eur. J., No. 19, 2013, pp. 12759-12770.
Marydasan, et al., "Dye encapsulation and release by a zinc-porphyrin pincer system through morphological transformations", RSC Adv., No. 3, Jan. 24, 2013, pp. 3815-3818.

*Primary Examiner* — Duc Truong
(74) *Attorney, Agent, or Firm* — Lewis Roca Rothgerber Christie LLP

(57) ABSTRACT

The present invention provides a metalporphyrin complex having structure represented by formula (I), wherein $R_1$, $R_2$, $R_3$, $R_4$, $R_5$, $R_6$, $R_7$, $R_8$, $R_9$ and $R_{10}$ are independently selected from one of hydrogen, halogen, aliphatic group, substituted heteroaliphatic group, aryl and substituted heteroaryl; n is 1-6; L is quaternary ammonium functional group or quaternary phosphonium functional group; M is a metal element; and X is one of halogen, $-NO_3$, $BF_4-$, $-CN$, p-methyl benzoate, o-nitrophenol oxygen anion, 2,4-dinitrophenol oxygen anion, 2,4,6-trinitrophenol oxygen anion, 3,5-dichlorophenol oxygen anion and pentafluorophenol oxygen anion. The metalporphyrin complex provided in the present invention has two quaternary ammonium functional groups or two quaternary phosphonium functional groups, and compared with the prior art, the metalporphyrin complex shows higher catalytic activity in catalyzing polymerization reaction of carbon dioxide and an epoxide.

12 Claims, No Drawings

METALPORPHYRIN COMPLEX, PREPARATION METHOD THEREFOR AND METHOD FOR PREPARING POLYCARBONATE

CROSS-REFERENCED TO RELATED APPLICATION(S)

This Application is a National Phase Patent Application and claims priority to and the benefit of International Application Number PCT/CN2013/085276, filed on Oct. 16, 2013, which claims priority to and the benefit of Chinese Patent Application No. 201310400892.X, filed Sep. 5, 2013, the entire contents of all of which are incorporated herein by reference.

FIELD OF THE INVENTION

The invention relates to the technical field of polymer, in particular to a metalporphyrin complex, a preparation method therefor and a method for preparing a polycarbonate.

BACKGROUND OF THE INVENTION

Polycarbonates, being macromolecular polymers having carbonate groups in molecular chains, are fully-degradable macromolecular material having good transparency and oxygen and water barrier properties, which have been applied to various fields such as bio-degradable pollution free material, novel liquid-crystal material, gas barrier material, rubber material reinforcing agent and composite material.

So far, methods for synthesizing polycarbonates include phosgene method, ring-opening polymerization of cyclic carbonate, transesterification of small molecular carbonate; and copolymerization of carbon dioxide and an epoxy compound. Preparation of polycarbonates by phosgene method using phosgene and diol as starting materials will adversely affect ecological environment due to the use of highly toxic chemical, i.e. phosgene as starting material; in preparation of polycarbonates via ring-opening polymerization of cyclic carbonates, polycarbonates having relatively high molecular weight can be synthesized by ring-opening polymerization of six- or higher-membered cyclic carbonates, but environmental problem also occurs since cyclic carbonates are mostly prepared by phosgene method; in preparation of polycarbonates by transesterification of small molecular carbonate, polycarbonates having various structures can be synthesized by transesterification of small molecular diol with small molecular carbonate; and when polycarbonates are prepared by copolymerization of carbon dioxide and an epoxy compound, carbon dioxide and an epoxy compound are polymerized in the presence of a catalyst to obtain the polycarbonates. Since carbon dioxide is the main gas causing greenhouse effect and also an inexpensive source of carbon and oxygen, preparation of polycarbonates using copolymerization of carbon dioxide and an epoxy compound has advantages in terms of environmental protection and economic efficiency, therefore preparation of polycarbonates using this method is of great interest.

Polycarbonates are synthesized by copolymerization of carbon dioxide and an epoxy compound in the presence of a catalyst, in which the catalyst employed includes a series of catalysts such as alkyl zinc-active hydrogen catalytic system, zinc carboxylate catalytic system, zinc phenolate catalytic system, zinc diimine catalytic system, bimetal cyanide catalytic system, rare-earth ternary catalytic system and metalporphyrin catalytic system. Metalporphyrin catalytic system draws attention in the field of carbon dioxide-epoxy compound catalysts because porphyrin ligand is simple to be prepared, and has special spatial configuration of electrons and relatively strong capability of coordinating with metals, for example, Chinese Patent Publication No. CN 102558199A discloses a metalporphyrin complex for catalyzing polymerization reaction of carbon dioxide and an epoxy compound to prepare a polycarbonate. However, the metalporphyrin complex disclosed in the prior art has relatively low catalytic activity when catalyzing copolymerization reaction of carbon dioxide and an epoxy compound.

SUMMARY OF THE INVENTION

In view of this, an object of the invention is to provide a metalporphyrin complex, which has relatively high catalytic activity when catalyzing copolymerization reaction of carbon dioxide and an epoxy compound.

The invention provides a metalporphyrin complex having a structure represented by Formula (I),

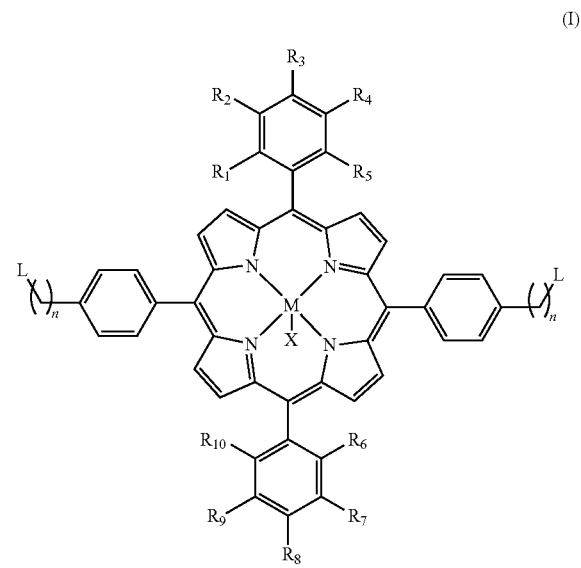

(I)

wherein $R_1$, $R_2$, $R_3$, $R_4$, $R_5$, $R_6$, $R_7$, $R_8$, $R_9$ and $R_{10}$ are independently one selected from the group consisting of hydrogen, halogen, an aliphatic group, a substituted heteroaliphatic group, an aryl group and a substituted heteroaryl group;

n is a degree of polymerization and ranges from 1 to 6;

L is one of a quaternary ammonium functional group and a quaternary phosphonium functional group;

M is a metal element; and

X is one selected from the group consisting of halogen, —$NO_3$, $CH_3COO$—, $CCl_3COO$—, $CF_3COO$—, $ClO_4$—, $BF_4$—, $BPh_4$—, —CN, —$N_3$, p-methyl benzoate, p-methyl benzenesulfonate, o-nitrophenolate anion, p-nitrophenolate anion, m-nitrophenolate anion, 2,4-dinitrophenolate anion, 3,5-dinitrophenolate anion, 2,4,6-trinitrophenolate anion, 3,5-dichlorophenolate anion, 3,5-difluorophenolate anion, 3,5-bis(trifluoromethyl)phenolate anion and pentafluorophenolate anion.

Preferably, L in the Formula (I) is one of a quaternary ammonium functional group having a structure represented by Formula (II) and a quaternary phosphonium functional group having a structure represented by Formula (III),

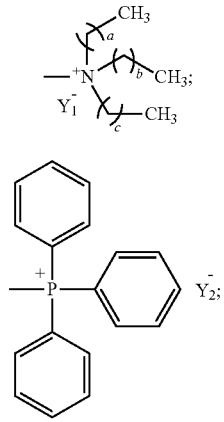
(II)

(III)

in Formula (II), a, b and c are degrees of polymerization and independently range from 1 to 6; and $Y_1^-$ in Formula (II) and $Y_2^-$ in Formula (III) are independently one selected from the group consisting of halogen anion, $NO_3^-$, $CH_3COO^-$, $CCl_3COO^-$, $CF_3COO^-$, $ClO_4^-$, $BF_4^-$, p-methyl benzoate, p-methyl benzenesulfonate, o-nitrophenolate anion, p-nitrophenolate anion, m-nitrophenolate anion, 2,4-dinitrophenolate anion, 3,5-dinitrophenolate anion, 2,4,6-trinitrophenolate anion, 3,5-dichlorophenolate anion, 3,5-difluorophenolate anion, 3,5-bis(trifluoromethyl)phenolate anion and pentafluorophenolate anion.

Preferably, $Y_1^-$ in the Formula (II) and $Y_2^-$ in the Formula (III) are independently one selected from the group consisting of halogen anion, $NO_3^-$, $CH_3COO^-$, $BF_4^-$, p-methyl benzoate, o-nitrophenolate anion, 2,4-dinitrophenolate anion, 2,4,6-trinitrophenolate anion, 3,5-dichlorophenolate anion and pentafluorophenolate anion.

Preferably, the $R_1$, $R_2$, $R_3$, $R_4$, $R_5$, $R_6$, $R_7$, $R_8$, $R_9$ and $R_{10}$ are independently one selected from the group consisting of hydrogen, halogen, an aliphatic group having a number of carbon atoms from 1 to 5, a substituted heteroaliphatic group having a number of Carbon atoms from 1 to 5 with oxygen as the heteroatom, an aryl group having a number of benzene rings from 1 to 3, and a halogen-substituted heteroaryl group having a number of benzene rings from 1 to 3.

Preferably, the M is one of iron element and aluminum element.

Preferably, the X is one selected from the group consisting of halogen, —$NO_3$, $CH_3COO$—, $BF_4$—, p-methyl benzoate, o-nitrophenolate anion, 2,4-dinitrophenolate anion, 2,4,6-trinitrophenolate anion, 3,5-dichlorophenolate anion and pentafluorophenolate anion.

The invention provides a method for preparing a metal-porphyrin complex including the following steps of:

step a), in which under an action of a catalyst, a first reaction between a first compound having a structure represented by Formula (1) and dichlorodimethyl methyl ether occurs in a solvent to obtain a second compound having a structure represented by Formula (2); and in the Formula (1), n ranges from 1 to 6, and Y is an anion in a quaternary ammonium functional group or the anion in a quaternary phosphonium functional group;

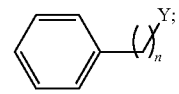
(1)

(2)

step b), in which a second reaction between a third compound having a structure represented by Formula (3) and pyrrole occurs under an action of indium chloride, and the resultant product from the second reaction and sodium hydroxide are subjected to a third reaction to obtain a fourth compound having a structure represented by Formula (4); and in the Formula (3), $R_1$, $R_2$, $R_3$, $R_4$ and $R_5$ are independently one selected from the group consisting of hydrogen, halogen, an aliphatic group, a substituted heteroaliphatic group, an aryl group and a substituted heteroaryl group;

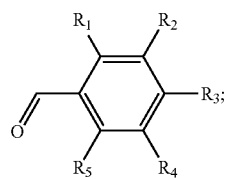
(3)

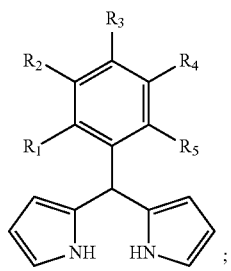
(4)

step c), in which a fourth reaction between a fifth compound having a structure represented by Formula (5) and pyrrole occurs under an action of indium chloride, and the resultant product from the fourth reaction and sodium hydroxide are subjected to a fifth reaction to obtain a sixth compound having a structure represented by Formula (6); and in the Formula (5), $R_6$, $R_7$, $R_8$, $R_9$ and $R_{10}$ are independently one selected from the group consisting of hydrogen, halogen, an aliphatic group, a substituted heteroaliphatic group, an aryl group and a substituted heteroaryl group;

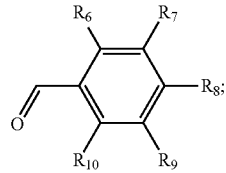
(5)

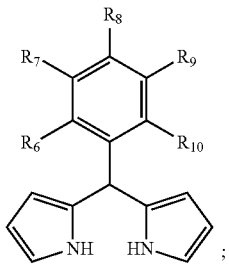

(6)

step d), in which under an action of a catalyst, the second compound obtained in the step a), the fourth compound obtained in the step b) and the sixth compound obtained in the step c) are subjected to a sixth reaction in a solvent, and the resultant product from the sixth reaction and 2,3-dichloro-5,6-dicyano-1,4-benzoquinone are subjected to a seventh reaction to obtain a seventh compound having a structure represented by Formula (7);

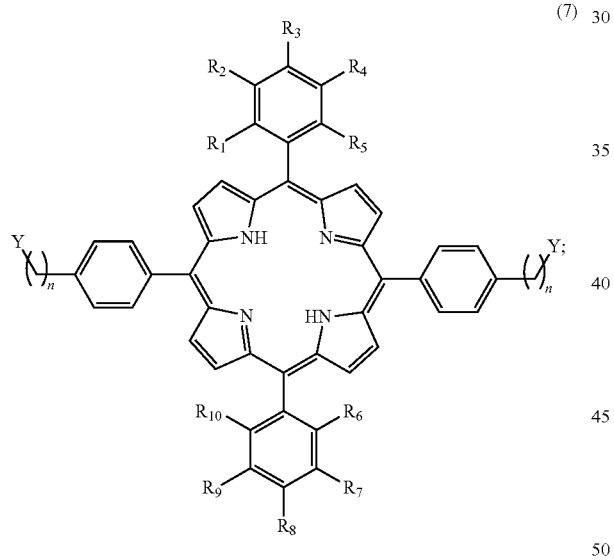

(7)

step e), in which an eighth reaction between the seventh compound obtained in the step d) and a metal salt compound occurs in a solvent to obtain an eighth compound having a structure represented by Formula (8); and in the Formula (8), M is a metal element, and X is one selected from the group consisting of halogen, —$NO_3$, $CH_3COO$—, $CCl_3COO$—, $CF_3COO$—, $ClO_4$—, $BF_4$—, $BPh_4$-, —CN, —$N_3$, p-methyl benzoate, p-methyl benzenesulfonate, o-nitrophenolate anion, p-nitrophenolate anion, m-nitrophenolate anion, 2,4-dinitrophenolate anion, 3,5-dinitrophenolate anion, 2,4,6-trinitrophenolate anion, 3,5-dichlorophenolate anion, 3,5-difluorophenolate anion, 3,5-bis(trifluoromethyl)phenolate anion and pentafluorophenolate anion;

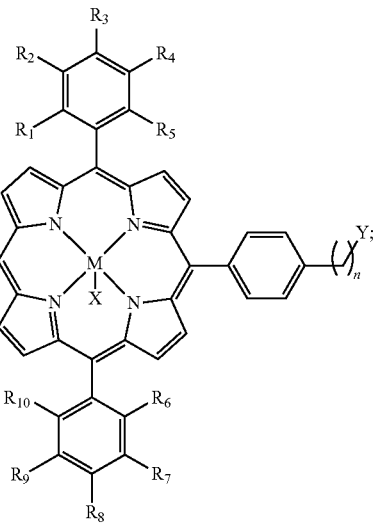

(8)

and step f), in which a ninth reaction between the eighth compound obtained in the step e) and a tertiary amine compound occurs in a solvent, or a tenth reaction between the eighth compound obtained in the step e) and a tertiary phosphine compound occurs in a solvent, to obtain the metalporphyrin complex having the structure represented by Formula (I); and L in the Formula (I) is one of a quaternary ammonium functional group and a quaternary phosphonium functional group;

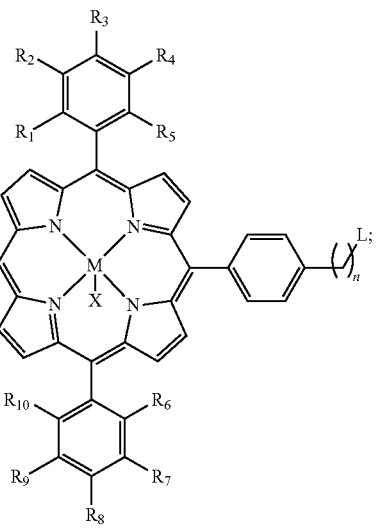

(I)

and the temporal sequence of the step a), step b) and step c) are not limited.

Preferably, a mass ratio of the catalyst, the first compound, dichlorodimethyl methyl ether and the solvent in the step a) is (1-5):(1-3):1:(15-25);

a mass ratio of the third compound, pyrrole, indium chloride and sodium hydroxide in the step b) is (4-7):(240-260):1:(15-25);

the molar ratio of the second compound, the fourth compound, the sixth compound, the catalyst, the solvent and 2,3-dichloro-5,6-dicyano-1,4-benzoquinone in the step d) is (0.5-1.5):1:(0.5-2):(2-4):(1200-1800):(1-3); and the molar ratio of the eighth compound, the tertiary amine compound and the solvent in the step f) is 1:(30-45):(120-160).

Preferably, the Y is one selected from the group consisting of halogen anion, $NO_3^-$, $CH_3COO^-$, $CCl_3COO^-$, $CF_3COO^-$, $ClO_4^-$, $BF_4^-$, p-methyl benzoate, p-methyl benzenesulfonate, o-nitrophenolate anion, p-nitrophenolate anion, m-nitrophenolate anion, 2,4-dinitrophenolate anion, 3,5-dinitrophenolate anion, 2,4,6-trinitrophenolate anion, 3,5-dichlorophenolate anion, 3,5-difluorophenolate anion, 3,5-bis(trifluoromethyl)phenolate anion and pentafluorophenolate anion;

the third compound or fifth compound is one selected from the group consisting of benzaldehyde, pentafluorobenzaldehyde, p-methyl benzaldehyde, p-ethoxy benzaldehyde, p-phenyl benzaldehyde and 3-chlorobiphenyl-4-benzaldehyde;

the tertiary amine compound is one of trimethylamine, tributylamine and trihexylamine; and the tertiary phosphine compound is triphenylphosphine.

Preferably, the first reaction is carried out at a temperature of 25 to 45° C. for a period of 20 to 40 min;

the second reaction is carried out at a temperature of 20 to 40° C. for a period of 1 to 3 h;

the third reaction is carried out at a temperature of 20 to 40° C. for a period of 30 to 60 min;

the sixth reaction is carried out at a temperature of 20 to 40° C. for a period of 0.5 to 1.5 h; and the seventh reaction is carried out at a temperature of 20 to 40° C. for a period of 0.5 to 1.5 h.

The invention provides a method for preparing a polycarbonate including the following steps of:

subjecting carbon dioxide and an epoxy compound to a polymerization reaction under an action of a catalyst to obtain the polycarbonate;

wherein the catalyst is the metalporphyrin complex in the technical solution described above or the metalporphyrin complex prepared by the method in the technical solution described above.

Preferably, a molar ratio of the catalyst to the epoxy compound is 1:(2500-100000);

a pressure of the polymerization reaction is from 0.1 to 5 MPa;

preferably, the polymerization reaction is carried out at a temperature ranging from 0 to 120° C.; and the duration of the polymerization reaction is from 0.5 to 48 h.

The invention provides a metalporphyrin complex having a structure represented by Formula (I), wherein $R_1$, $R_2$, $R_3$, $R_4$, $R_5$, $R_6$, $R_7$, $R_8$, $R_9$ and $R_{10}$ are independently one selected from the group consisting of hydrogen, halogen, an aliphatic group, a substituted heteroaliphatic group, an aryl group and a substituted heteroaryl group; n is a degree of polymerization and ranges from 1 to 6; L is one of a quaternary ammonium functional group and a quaternary phosphonium functional group; M is a metal element; and X is one selected from the group consisting of halogen, $-NO_3$, $CH_3COO-$, $CCl_3COO-$, $CF_3COO-$, $ClO_4-$, $BF_4-$, $BPh_4-$, $-CN$, $-N_3$, p-methyl benzoate, p-methyl benzenesulfonate, o-nitrophenolate anion, p-nitrophenolate anion, m-nitrophenolate anion, 2,4-dinitrophenolate anion, 3,5-dinitrophenolate anion, 2,4,6-trinitrophenolate anion, 3,5-dichlorophenolate anion, 3,5-difluorophenolate anion, 3,5-bis(trifluoromethyl)phenolate anion and pentafluorophenolate anion. In the invention, the metalporphyrin complex contains two quaternary ammonium functional groups or two quaternary phosphonium functional groups, and possesses higher catalytic activity compared with those of the prior art when catalyzing the polymerization reaction of carbon dioxide and the epoxy compound. Further, in catalyzing the polymerization reaction of carbon dioxide and the epoxy compound, the metalporphyrin complex provided according to the invention has higher product selectivity, produces less cyclic carbonate byproducts, and results in the obtained polycarbonate having a higher number average molecular weight. The experimental results demonstrate that when the metalporphyrin complex provided according to the invention is employed to catalyze the polymerization reaction of carbon dioxide and an epoxy compound, the turnover frequency (TOF) of the catalytic system may be up to 4610 $h^-$; in the obtained polymer, the cyclic carbonate byproducts are less than 5.0%, while the content of carbonate unit is higher than 99%; and the obtained polycarbonate has a number average molecular weight up to 135000.

DETAILED DESCRIPTION

The invention provides a metalporphyrin complex having a structure represented by Formula (I):

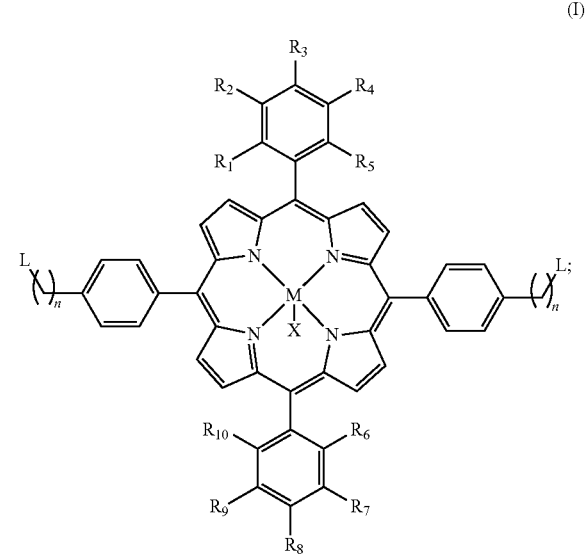

(I)

wherein $R_1$, $R_2$, $R_3$, $R_4$, $R_5$, $R_6$, $R_7$, $R_8$, $R_9$ and $R_{10}$ are independently one selected from the group consisting of hydrogen, halogen, an aliphatic group, a substituted heteroaliphatic group, an aryl group and a substituted heteroaryl group; preferably, independently one selected from the group consisting of hydrogen, halogen, an aliphatic group having a number of carbon atoms from 1 to 5, a substituted heteroaliphatic group having a number of carbon atoms from 1 to 5 with oxygen as the heteroatom, an aryl group having a number of benzene rings from 1 to 3, and a halogen-substituted heteroaryl group having a number of benzene rings from 1 to 3; and more preferably, independently one selected from the group consisting of hydrogen, fluorine, chlorine, iodine, methyl, ethyl, propyl, methoxy, ethoxy, propoxy, phenyl, biphenyl and chlorophenyl; and most preferably, independently one selected from the group consisting of hydrogen, fluorine, methyl, ethoxy, phenyl and 3-chlorophenyl;

n is a degree of polymerization and ranges from 1 to 6, preferably from 2 to 5, and more preferably is 3;

L is one of a quaternary ammonium functional group and a quaternary phosphonium functional group; preferably one of a quaternary ammonium functional group having a structure represented by Formula (II) and a quaternary phosphonium functional group having a structure represented by Formula (III),

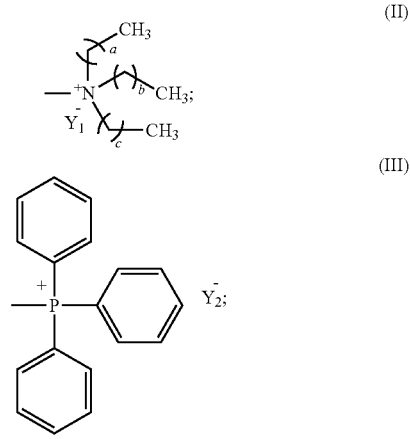

in Formula (II), a, b and c are degrees of polymerization, and a, b and c are independently selected from 1 to 6, preferably independently selected from 2 to 5, and more preferably are all 4;

$Y_1^-$ in Formula (II) and $Y_2^-$ in Formula (III) are independently one selected from the group consisting of halogen anion, $NO_3^-$, $CH_3COO^-$, $CCl_3COO^-$, $CF_3COO^-$, $ClO_4^-$, $BF_4^-$, p-methyl benzoate, p-methyl benzenesulfonate, o-nitrophenolate anion, p-nitrophenolate anion, m-nitrophenolate anion, 2,4-dinitrophenolate anion, 2,4,6-trinitrophenolate anion, 3,5-dichlorophenolate anion, 3,5-difluorophenolate anion, 3,5-bis(trifluoromethyl)phenolate anion and pentafluorophenolate anion; preferably, independently one selected from the group consisting of halogen anion, $NO_3^-$, $CH_3COO^-$, $BF_4^-$, p-methyl benzoate, o-nitrophenolate anion, 2,4-dinitrophenolate anion, 2,4,6-trinitrophenolate anion, 3,5-dichlorophenolate anion and pentafluorophenolate anion; more preferably, independently one selected from the group consisting of halogen anion, $NO_3^-$ and $BF_4^-$, and most preferably, independently one selected from the group consisting of $I^-$, $NO_3^-$ and $BF_4^-$;

M is a metal element and preferably one of aluminum element and iron element. In the invention, the metalporphyrin complex preferably has an inexpensive, green and environmentally friendly aluminum element or iron element as the active center, and the polycarbonate prepared by catalyzing the polymerization reaction of carbon dioxide and an epoxy compound with this metalporphyrin complex is free of toxic metals that can be directly used without the need of removing the catalyst, thus effectively solving the problem of residual toxic metals in the polycarbonate material.

X is one selected from the group consisting of halogen, $-NO_3$, $CH_3COO-$, $CCl_3COO-$, $CF_3COO-$, $ClO_4-$, $BF_4-$, $BPh_4-$, $-CN$, $-N_3$, p-methyl benzoate, p-methyl benzenesulfonate, o-nitrophenolate anion, p-nitrophenolate anion, m-nitrophenolate anion, 2,4-dinitrophenolate anion, 3,5-dinitrophenolate anion, 2,4,6-trinitrophenolate anion, 3,5-dichlorophenolate anion, 3,5-difluorophenolate anion, 3,5-bis(trifluoromethyl)phenolate anion and pentafluorophenolate anion; preferably one selected from the group consisting of halogen, $-NO_3$, $CH_3COO-$, $BF_4-$, p-methyl benzoate, o-nitrophenolate anion, 2,4-dinitrophenolate anion, 2,4,6-trinitrophenolate anion, 3,5-dichlorophenolate anion and pentafluorophenolate anion; more preferably one of halogen, $-NO_3$ and $BF_4-$, and most preferably one of $-Cl$, $-NO_3$ and $BF_4-$.

The metalporphyrin complex provided according to the invention comprises two quaternary ammonium functional groups or two quaternary phosphonium functional groups, and has higher catalytic activity compared with those of the prior art when catalyzing the polymerization reaction of carbon dioxide and an epoxy compound. Further, in catalyzing the polymerization reaction of carbon dioxide and the epoxy compound, the metalporphyrin complex provided according to the invention has higher product selectivity, produces less cyclic carbonate byproducts, and results in the obtained polycarbonate having a higher number average molecular weight.

In the invention, in the case that in Formula (I) $R_1$, $R_2$, $R_3$, $R_4$, $R_5$, $R_6$, $R_7$, $R_8$, $R_9$ and $R_{10}$ are hydrogen, n is 3, M is Al element, X is $Cl-$, and L is a quaternary ammonium functional group having a structure represented by Formula (II) with a is 4 and $Y_1^-$ is $I^-$ in Formula (II), the metalporphyrin complex has a structure represented by Formula (IV):

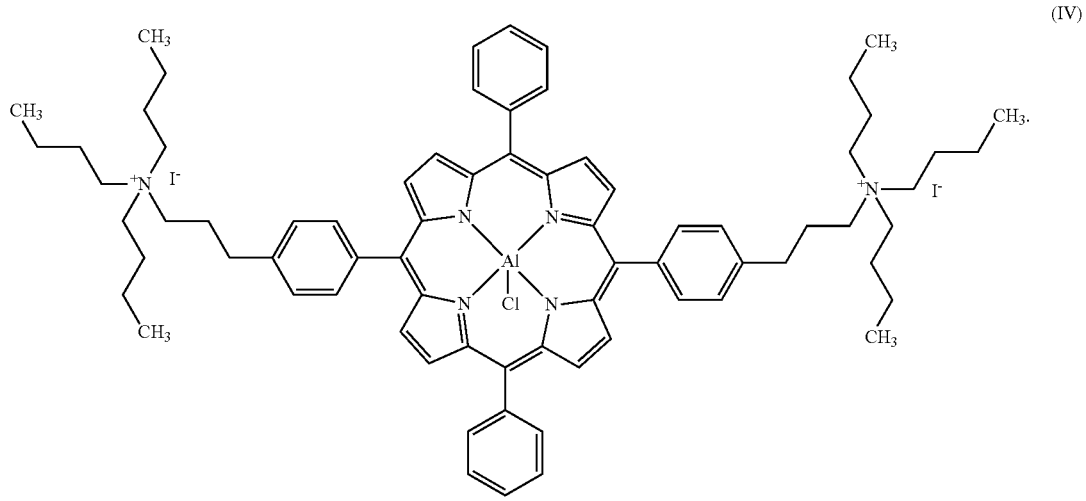

In the invention, in the case that in Formula (I) $R_1$, $R_2$, $R_3$, $R_4$, $R_5$, $R_6$, $R_7$, $R_8$, $R_9$ and $R_{10}$ are fluorine, n is 6, M is Al element, X is Cl—, and L is a quaternary ammonium functional group having a structure represented by Formula (II) with a is 1 and $Y_1^-$ is $I^-$ in Formula (II), the metalporphyrin complex has a structure represented by Formula (V):

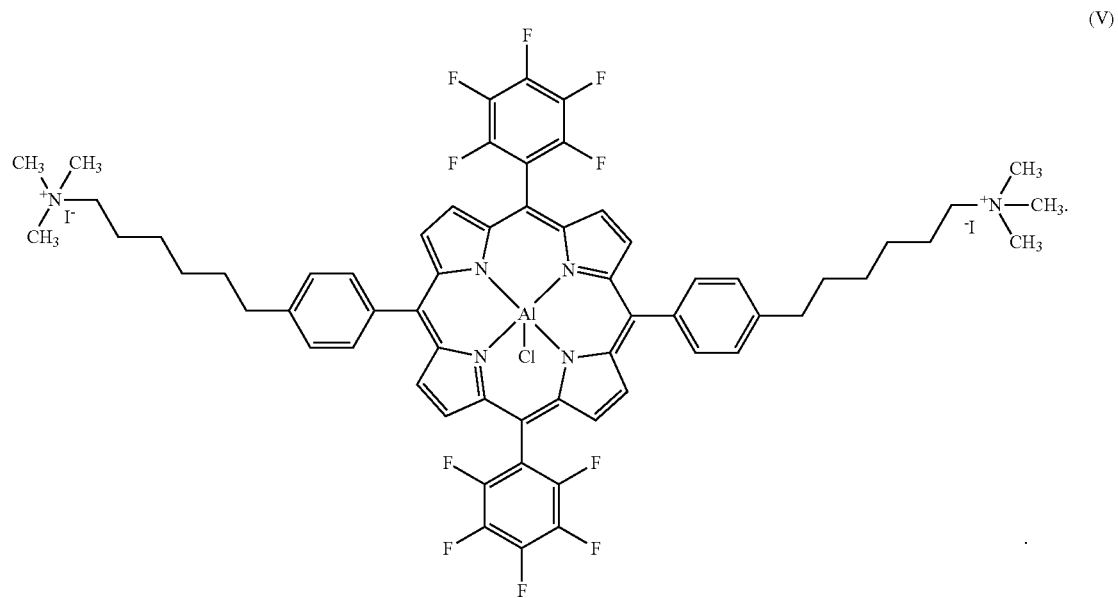

(V)

In the invention, in the case that in Formula (I) $R_1$, $R_2$, $R_4$, $R_5$, $R_6$, $R_7$, $R_9$ and $R_{10}$ are hydrogen, $R_3$ and $R_8$ are methyl, n is 3, M is Al element, X is Cl—, and L is a quaternary ammonium functional group having a structure represented by Formula (II) with a is 6 and $Y_1^-$ is $I^-$ in Formula (II), the metalporphyrin complex has a structure represented by Formula (VI):

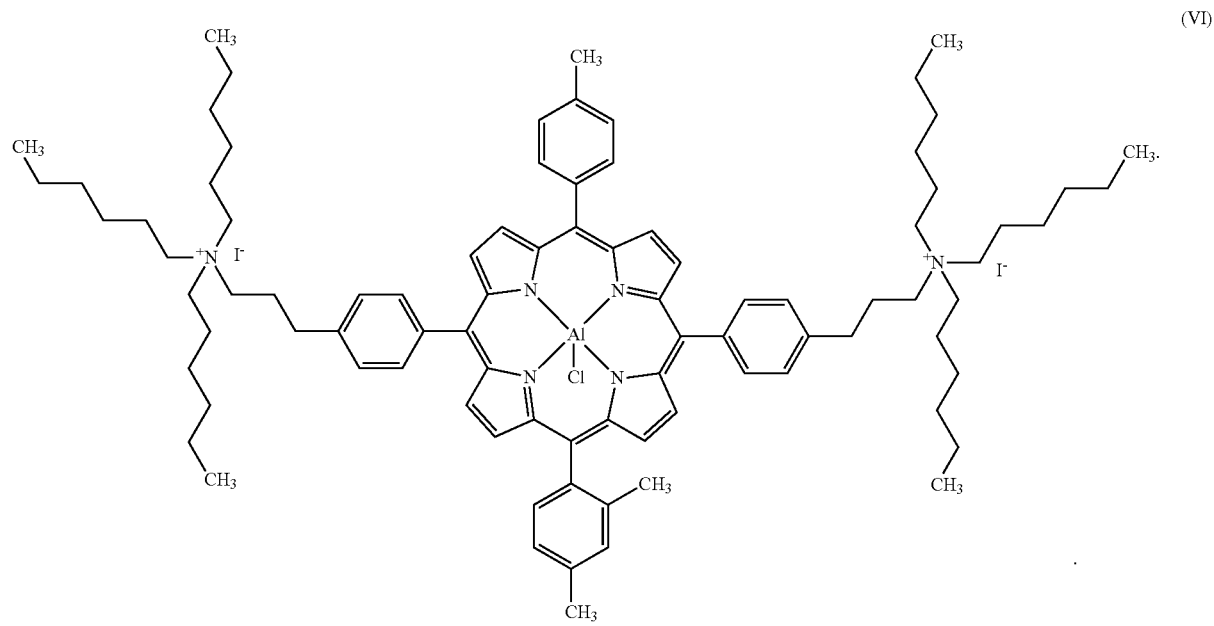

(VI)

In the invention, in the case that in Formula (I) $R_1$, $R_2$, $R_4$, $R_5$, $R_6$, $R_7$, $R_9$ and $R_{10}$ are hydrogen, $R_3$ and $R_8$ are ethoxy, n is 1, M is Fe element, X is $BF_4^-$, and L is a quaternary ammonium functional group having a structure represented by Formula (II) with a is 4 and $Y_1^-$ is $BF_4^-$ in Formula (II), the metalporphyrin complex has a structure represented by Formula (VII):

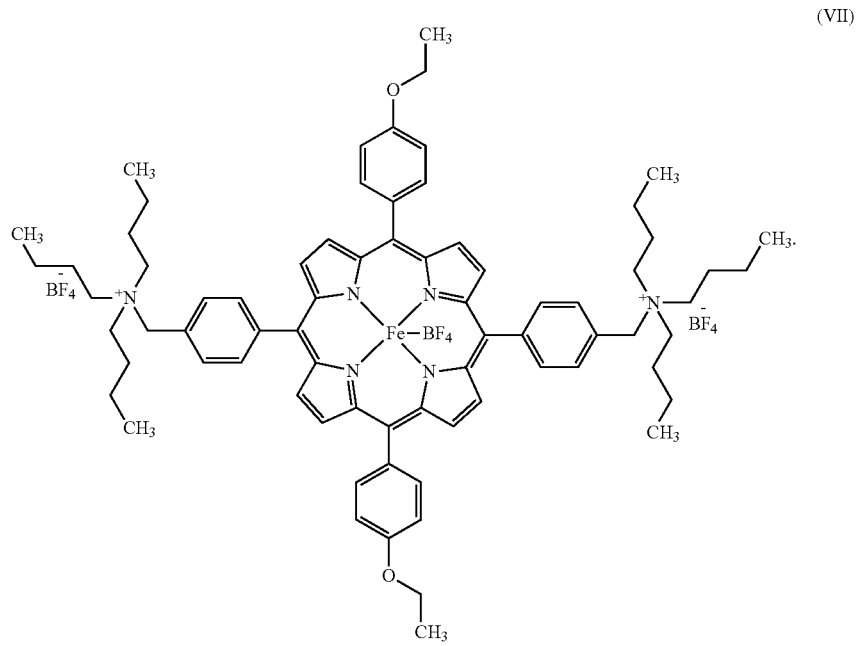

(VII)

In the invention, in the case that in Formula (I) $R_1$, $R_2$, $R_4$, $R_5$, $R_6$, $R_7$, $R_9$ and $R_{10}$ are hydrogen, $R_3$ and $R_8$ are phenyl, n is 3, M is Fe element, X is $-NO_3$, and L is a quaternary ammonium functional group having a structure represented by Formula (II) with a is 4 and $Y_1^-$ is $NO_3^-$ in Formula (II), the metalporphyrin complex has a structure represented by Formula (VIII):

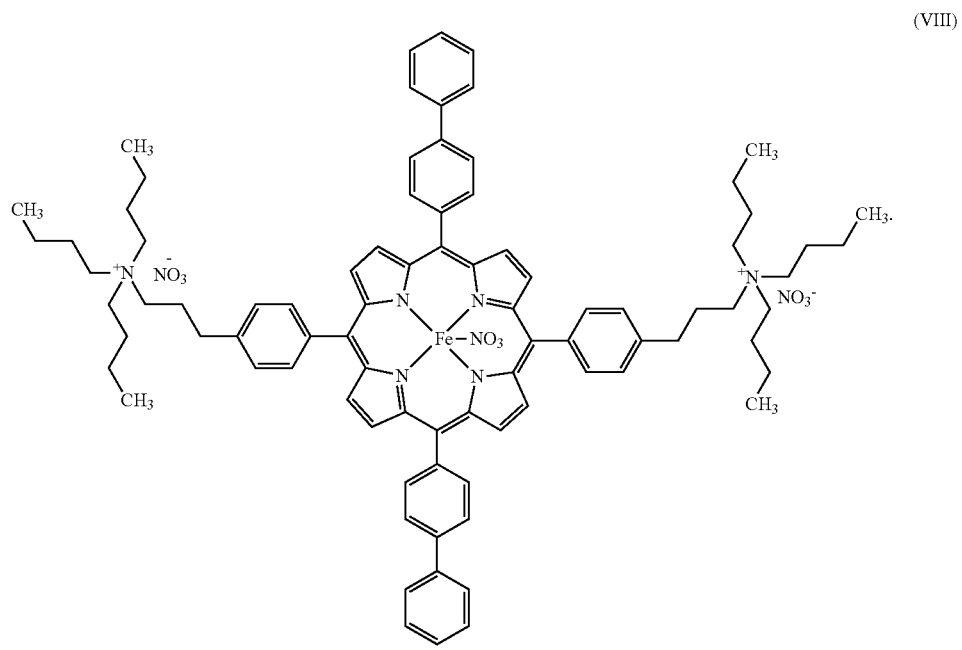

(VIII)

In the invention, in the case that in Formula (I) $R_1$, $R_2$, $R_4$, $R_5$, $R_6$, $R_7$, $R_9$ and $R_{10}$ are hydrogen, $R_3$ and $R_8$ are 3-chlorophenyl, n is 3, M is Fe element, X is $-NO_3$, and L is a quaternary ammonium functional group having a structure represented by Formula (II) with a is 4 and $Y_1^-$ is $NO_3^-$ in Formula (II), the metalporphyrin complex has a structure represented by Formula (IX):

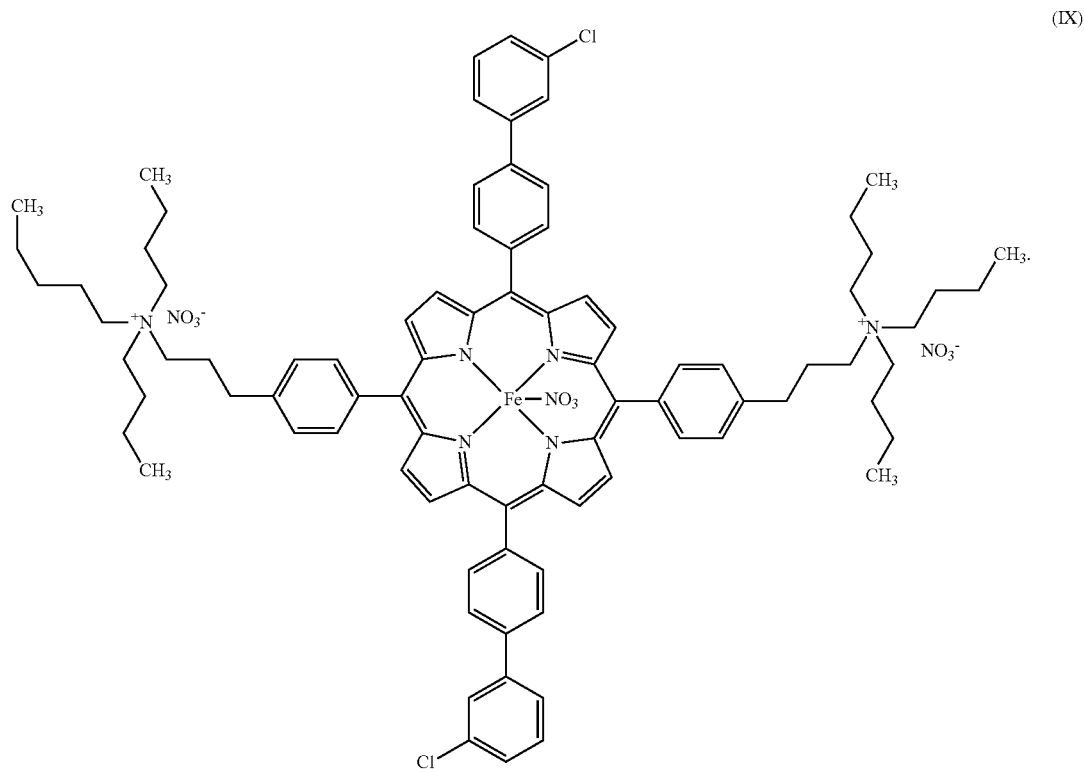

(IX)

In the invention, in the case that in Formula (I) $R_1$, $R_2$, $R_3$, $R_4$, $R_6$, $R_7$, $R_8$, $R_9$ and $R_{10}$ are hydrogen, n is 3, M is Al element, X is Cl—, and L is a quaternary phosphonium functional group having a structure represented by Formula (III) with $Y_2^-$ is $I^-$ in Formula (III), the metalporphyrin complex has a structure represented by Formula (X):

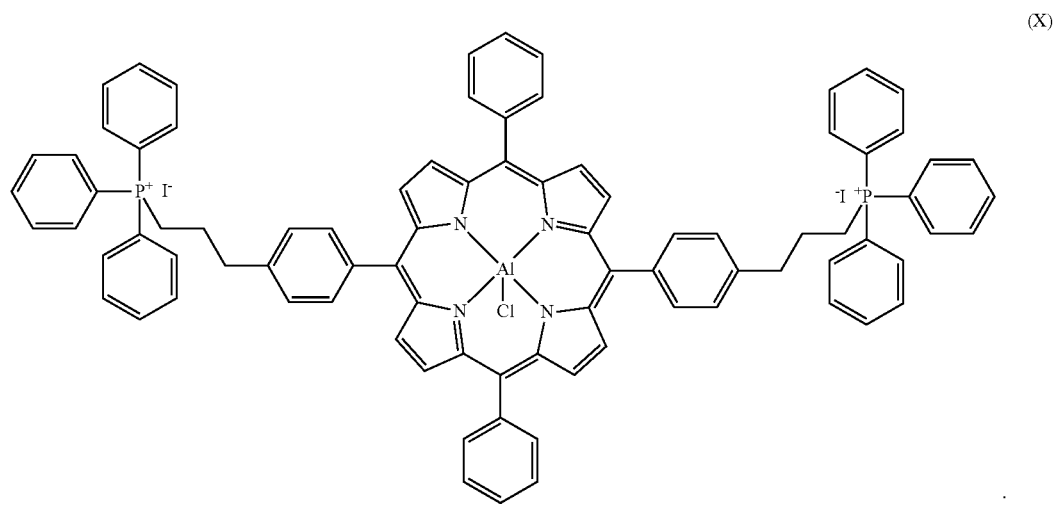

(X)

The invention provides a method for preparing a metal-porphyrin complex including the following steps:

step a), in which under an action of a catalyst, a first reaction between a first compound having a structure represented by Formula (1) and dichlorodimethyl methyl ether occurs in a solvent to obtain a second compound having a structure represented by Formula (2); and in the Formula (1), n ranges from 1 to 6, and Y is an anion in a quaternary ammonium functional group or the anion in a quaternary phosphonium functional group;

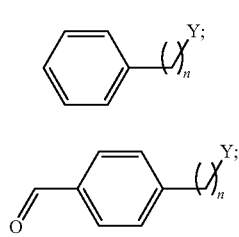

(1)

(2)

step b), in which a second reaction between a third compound having a structure represented by Formula (3) and pyrrole occurs under an action of indium chloride, and the resultant product from the second reaction and sodium hydroxide are subjected to a third reaction to obtain a fourth compound having a structure represented by Formula (4); and in the Formula (3), $R_1$, $R_2$, $R_3$, $R_4$ and $R_5$ are independently one selected from the group consisting of hydrogen, halogen, an aliphatic group, a substituted heteroaliphatic group, an aryl group and a substituted heteroaryl group;

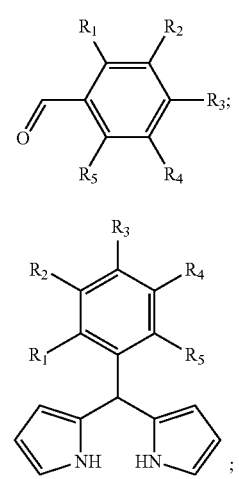

(3)

(4)

step c), in which a fourth reaction between a fifth compound having a structure represented by Formula (5) and pyrrole occurs under an action of indium chloride, and the resultant product from the fourth reaction and sodium hydroxide are subjected to a fifth reaction to obtain a sixth compound having a structure represented by Formula (6); and in the Formula (5), $R_6$, $R_7$, $R_8$, $R_9$ and $R_{10}$ are independently one selected from the group consisting of hydrogen, halogen, an aliphatic group, a substituted heteroaliphatic group, an aryl group and a substituted heteroaryl group;

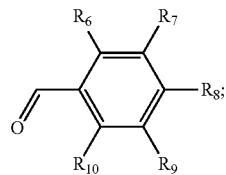

(5)

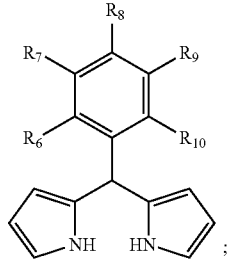

(6)

step d), in which under an action of a catalyst, the second compound obtained in the step a), the fourth compound obtained in the step b) and the sixth compound obtained in the step c) are subjected to a sixth reaction in a solvent, and the resultant product from the sixth reaction and 2,3-dichloro-5,6-dicyano-1,4-benzoquinone are subjected to a seventh reaction to obtain a seventh compound having a structure represented by Formula (7);

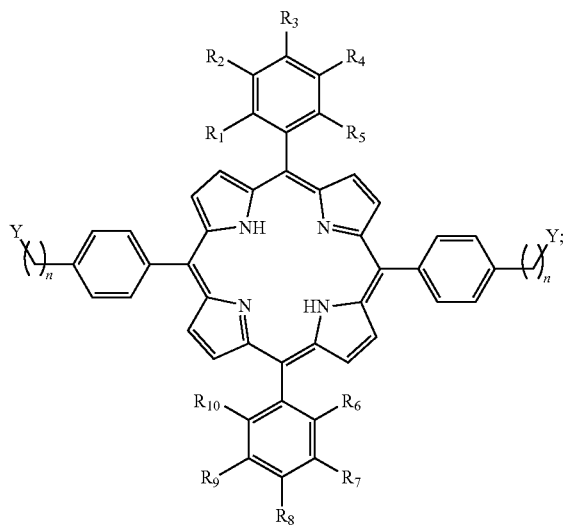

(7)

step e), in which an eighth reaction between the seventh compound obtained in the step d) and a metal salt compound occurs in a solvent to obtain an eighth compound having a structure represented by Formula (8); and in the Formula (8), M is a metal element, and X is one selected from the group consisting of halogen, —$NO_3$, $CH_3COO$—, $CCl_3COO$—, $CF_3COO$—, $ClO_4$—, $BF_4$—, $BPh_4$-, —CN, —$N_3$, p-methyl benzoate, p-methyl benzenesulfonate, o-nitrophenolate anion, p-nitrophenolate anion, m-nitrophenolate anion, 2,4-dinitrophenolate anion, 3,5-dinitrophenolate anion, 2,4,6-trinitrophenolate anion, 3,5-dichlorophenolate anion, 3,5-difluorophenolate anion, 3,5-bis(trifluoromethyl)phenolate anion and pentafluorophenolate anion;

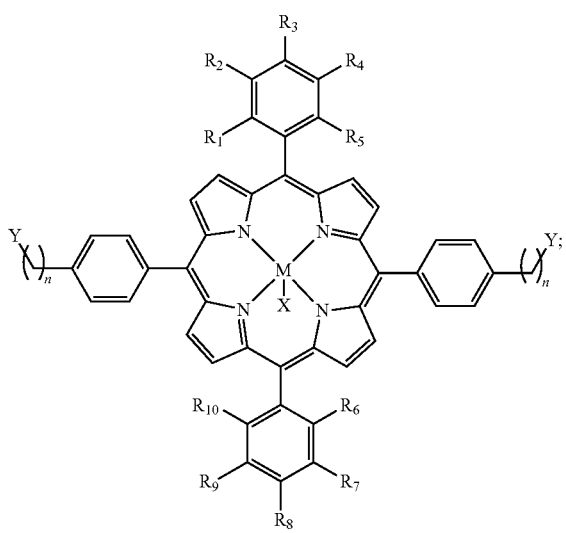

(8)

and step f), in which a ninth reaction between the eighth compound obtained in the step e) and a tertiary amine compound occurs in a solvent, or a tenth reaction between the eighth compound obtained in the step e) and a tertiary phosphine compound occurs in a solvent, to obtain the metalporphyrin complex having the structure represented by Formula (I); and L in the Formula (I) is one of a quaternary ammonium functional group and a quaternary phosphonium functional group;

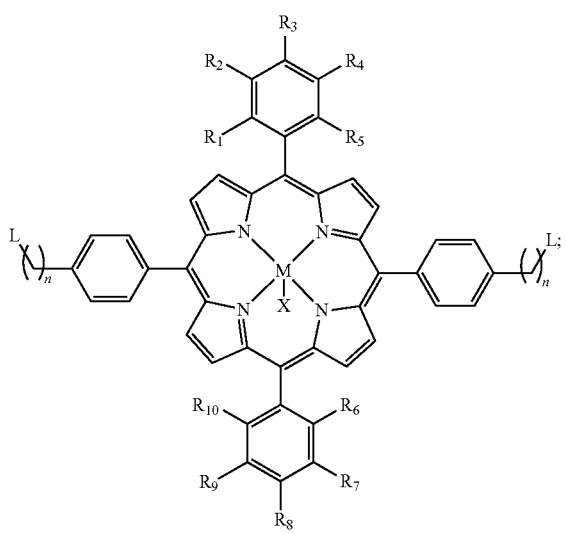

(I)

and the temporal sequence of the step a), step b) and step c) according to the invention are not limited.

In the invention, under an action of a catalyst, the first reaction between the first compound having the structure represented by Formula (1) and dichlorodimethyl methyl ether occurs in the solvent to obtain the second compound having the structure represented by Formula (2). In the invention, the catalyst in the step a) is preferably titanium tetrachloride; n in the Formula (1) is the same as that in the technical solutions described above and the details thereof are omitted here; Y in the Formula (1) is the anion in the quaternary ammonium functional group or the anion in the quaternary phosphonium functional group, and is preferably one selected from the group consisting of halogen anion, $NO_3^-$, $CH_3COO^-$, $CCl_3COO^-$, $CF_3COO^-$, $ClO_4^-$, $BF_4^-$, p-methyl benzoate, p-methyl benzenesulfonate, o-nitrophenolate anion, p-nitrophenolate anion, m-nitrophenolate anion, 2,4-dinitrophenolate anion, 3,5-dinitrophenolate anion, 2,4,6-trinitrophenolate anion, 3,5-dichlorophenolate anion, 3,5-difluorophenolate anion, 3,5-bis(trifluoromethyl)phenolate anion and pentafluorophenolate anion, more preferably one selected from the group consisting of halogen anion, $NO_3^-$, $CH_3COO^-$, $BF_4^-$, p-methyl benzoate, o-nitrophenolate anion, 2,4-dinitrophenolate anion, 2,4,6-trinitrophenolate anion, 3,5-dichlorophenolate anion, and pentafluorophenolate anion, and most preferably one selected from the group consisting of halogen anion, $NO_3^-$ and $BF_4^-$; the solvent in the step (a) is preferably dichloromethane, and more preferably dry dichloromethane; a mass ratio of the catalyst, the first compound, dichlorodimethyl methyl ether and the solvent in the step a) is preferably (1-5):(1-3):1:(15-25), more preferably (2-4):(1-3):1:(18-23), and most preferably 3:2:1:20. The source of the first compound is not particularly limited in the invention, and the first compound may be commercially available, or may be prepared according to the preparation methods well known by those skilled in the art, depending on the various options for n and Y in the Formula (1). In the invention, when Y is $Br^-$ and n is from 1 to 6 in the Formula (1), the first compound has a structure represented by Formula (9), which may be commercially available;

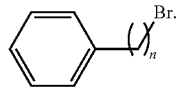

(9)

In the invention, when Y is $I^-$ and n is from 1 to 6 in the Formula (1), the first compound has a structure represented by Formula (10);

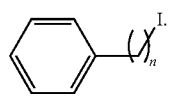

(10)

In the invention, the first compound having the structure represented by Formula (10) may be prepared according to the following method:

the first compound having the structure represented by Formula (9) is reacted with an alkali metal iodide in a solvent to obtain the first compound having the structure represented by Formula (10). According to the invention, the alkali metal iodide is preferably sodium iodide or potassium iodide; according to the invention, in the process for preparing the first compound having the structure represented by Formula (10), the solvent is preferably acetonitrile, and more preferably dry acetonitrile; a mass ratio of the first compound having the structure represented by Formula (9), the alkali metal iodide and the solvent is preferably 1:(5-8):(4-7), more preferably 1:(6-7):(5-6), and most preferably 1:6.6:5.1.

In the invention, preferably, the first compound having the structure represented by Formula (9) is mixed with the alkali metal iodide in a solvent and reacted through reflux condensation to obtain the first compound having the structure represented by Formula (10). According to the invention, in the process for preparing the first compound having the structure represented by Formula (10), the duration of the reflux condensation is preferably 20 to 26 h, more preferably 21 to 25 h, and most preferably 24 h.

According to the invention, after the reaction between the first compound having the structure represented by Formula (9) and the alkali metal iodide is complete, preferably, the resultant reaction solution is extracted, and then the resultant extracted organic phase is dried to obtain the first compound having the structure represented by Formula (10); and more preferably, water is added to the resultant reaction solution, then the reaction solution is mixed with an extracting agent for extracting the reaction product to obtain an organic phase. According to the invention, in the process for preparing the first compound having the structure represented by Formula (10), the extracting agent employed for the extraction is preferably an ether compound, and more preferably ethyl ether; and the drying agent employed for the drying is preferably anhydrous magnesium sulfate.

According to the invention, when the Y is other anions than Br$^-$ and I$^-$ described above, the first compound having the structure represented by Formula (1) may be prepared using the method described above for preparing the first compound having the structure represented by Formula (10) with the corresponding anion to substitute Br$^-$ in the first compound having the structure represented by Formula (9). The substitute process is not particularly limited in the invention, and may be carried out using the method for substituting Br$^-$ well known by those skilled in the art in any step of the process for preparing the metalporphyrin complex having the structure represented by Formula (I).

According to the invention, after the first compound having the structure represented by Formula (1) is obtained, preferably, the first compound is first added to a solvent and then the resultant solution of the first compound is mixed with dichlorodimethyl methyl ether to carry out the first reaction, resulting in the second compound having the structure represented by Formula (2); and more preferably, the first compound is added to a solvent in an ice bath to obtain a solution of the first compound, and dichlorodimethyl methyl ether is then added to the solution of the first compound to carry out the first reaction, resulting in the second compound having the structure represented by Formula (2). According to the invention, dichlorodimethyl methyl ether is preferably added to the solution of the first compound within 20 to 40 min, more preferably within 25 to 35 min, and most preferably within 30 min. In the present invention, the first reaction is carried out preferably at a temperature of 25 to 45° C., more preferably 30 to 40° C., and most preferably 35° C. for preferably 20 to 40 min, more preferably 25 to 35 min, and most preferably 30 min;

According to the invention, after the reaction between the first compound and dichlorodimethyl methyl ether is complete, preferably, the resultant reaction product is extracted, and then the resultant extracted organic phase is washed and purified to obtain the pure second compound; and more preferably, the resultant reaction product is poured into a vessel containing ice blocks, and then the reaction product is mixed with an extracting agent for extracting the reaction product to obtain an organic phase. In the invention, the extracting agent employed for the extraction in the step a) is preferably dichloromethane; the washing agent employed for the washing in the step a) is preferably sodium bicarbonate; the washed organic phase is preferably purified using silica gel column; and the eluent employed during the process of the silica gel column purification in the step a) is preferably petroleum ether and dichloromethane, more preferably petroleum ether and dichloromethane at a mass ratio of 1:(1-3), and most preferably petroleum ether and dichloromethane at a mass ratio of 1:2.

According to the invention, the second reaction between the third compound having the structure represented by Formula (3) and pyrrole occurs under an action of indium chloride, and then the resultant product from the second reaction and sodium hydroxide are subjected to the third reaction to obtain the fourth compound having the structure represented by Formula (4). In the invention, $R_1$, $R_2$, $R_3$, $R_4$ and $R_5$ in the Formula (3) are the same as $R_1$, $R_2$, $R_3$, $R_4$ and $R_5$ in the technical solution described above and the details thereof are omitted here. Preferably, when $R_1$, $R_2$, $R_3$, $R_4$ and $R_5$ are all hydrogen, the third compound is benzaldehyde; when $R_1$, $R_2$, $R_3$, $R_4$ and $R_5$ are all fluorine, the third compound is pentafluorobenzaldehyde; when $R_1$, $R_2$, $R_4$ and $R_5$ are all hydrogen but $R_3$ is methyl, the third compound is p-methyl benzaldehyde; when $R_1$, $R_2$, $R_4$ and $R_5$ are all hydrogen but $R_3$ is ethoxy, the third compound is p-ethoxy benzaldehyde; when $R_1$, $R_2$, $R_4$ and $R_5$ are all hydrogen and $R_3$ is phenyl, the third compound is p-phenyl benzaldehyde; when $R_1$, $R_2$, $R_4$ and $R_5$ are all hydrogen but $R_3$ is 3-chlorophenyl, the third compound is 3-chlorobiphenyl-4-benzaldehyde; the pyrrole is preferably dry pyrrole; and the sodium hydroxide is preferably powdered sodium hydroxide. A mass ratio of the third compound, pyrrole, indium chloride and sodium hydroxide is preferably (4-7):(240-260):1:(15-25), more preferably (5-6):(245-255):1:(18-22), and most preferably 5.3:253:1:20. The source of the third compound is not particularly limited in the invention, and the third compound may be commercially available depending on the various options for $R_1$, $R_2$, $R_3$, $R_4$ and $R_5$ in the Formula (3).

According to the invention, preferably, the third compound having the structure represented by Formula (3) is added to pyrrole, then the second reaction occurs under an action of indium chloride, and the resultant product from the second reaction and sodium hydroxide are further subjected to the third reaction to obtain the fourth compound having the structure represented by Formula (4); and more preferably, indium chloride is added to the mixed system of the third compound and pyrrole to carry out the second reaction, and after the second reaction is complete, sodium hydroxide is added to the resultant product from the second reaction to carry out the third reaction, resulting in the fourth compound having the structure represented by Formula (4). In the invention, the second reaction is carried out preferably at a temperature of 20 to 40° C., and more preferably 25 to 35° C. for preferably 1 to 3 h, and more preferably 2 h; and the third reaction is carried out preferably at a temperature of 20 to 40° C., and more preferably 25-35° C. for preferably 30 to 60 min, more preferably 40 to 50 min and most preferably 45 min.

According to the invention, after the third reaction is complete, preferably, the resultant product from the third reaction is filtered, then the filtrate is dried to obtain a crude product of the fourth compound, and the crude product is purified to obtain the pure fourth compound. The filtration method in the step b) is not particularly limited in the invention and may be technical solutions for filtration well known by those skilled in the art. The drying method in the step b) is not particularly limited in the invention and preferably the filtrate is dried by evaporation, where the method for drying by evaporation is not particularly limited in the invention and may be technical solutions for drying by evaporation well known by those skilled in the art. According to the invention, the crude product of the fourth compound is preferably purified using silica gel column; and in the invention, the eluent employed during the process of the silica gel column purification in the step b) is preferably petroleum ether and dichloromethane, more preferably petroleum ether and dichloromethane at a mass ratio of 1:(1-3), and most preferably petroleum ether and dichloromethane at a mass ratio of 1:2.

According to the invention, the fourth reaction between the fifth compound having the structure represented by Formula (5) and pyrrole occurs under an action of indium chloride, then the resultant product from the fourth reaction and sodium hydroxide are subjected to the fifth reaction to obtain the sixth compound having the structure represented by Formula (6). In the invention, $R_6$, $R_7$, $R_8$, $R_9$ and $R_{10}$ in the Formula (5) are the same as $R_6$, $R_7$, $R_8$, $R_9$ and $R_{10}$ in the technical solution described above and the details thereof are omitted here; the kind and source of the fifth compound are the same as those of the third compound in the technical solution described above and the details thereof are omitted here; preferably, the method for preparing the fourth compound in the technical solution described above is preferably employed to prepare the sixth compound in the invention, and the details thereof are omitted here.

According to the invention, after the second compound, the fourth compound and the sixth compound are obtained, the second compound, the fourth compound and the sixth compound are subjected to the sixth reaction in a solvent, and then the resultant product from the sixth reaction and DDQ are subjected to the seventh reaction to obtain the seventh compound having the structure represented by Formula (7). In the invention, the catalyst in the step d) is preferably trifluoroacetic acid; the solvent in the step d) is preferably dichloromethane and more preferably dry dichloromethane; and the molar ratio of the second compound, the fourth compound, the sixth compound, the catalyst, the solvent and DDQ in the step d) is preferably (0.5-1.5):1:(0.5-2):(2-4):(1200-1800):(1-3), more preferably (0.8-1.2):1:(0.8-1.2):(2.5-3.5):(1400-1600):(1.5-2.5), and most preferably 0.9:1:1:2.8:1500:2.

According to the invention, preferably, under an action of a catalyst, the second compound, the fourth compound and the sixth compound are added to a solvent to carry out the sixth reaction, and then the resultant product from the sixth reaction and DDQ are subjected to the seventh reaction to obtain the seventh compound having the structure represented by Formula (7); and more preferably, the second compound, the fourth compound and the sixth compound are added to a solvent to obtain a mixed solution, then the catalyst is added to the mixed solution to carry out the sixth reaction, and after the sixth reaction is complete, DDQ is added to the resultant product from the sixth reaction to carry out the seventh reaction, resulting in the seventh compound having the structure represented by Formula (7). In the invention, the sixth reaction is carried out preferably at a temperature of 20 to 40° C., and more preferably 25 to 35° C. for preferably 0.5 to 1.5 h, and more preferably 1 h; and the seventh reaction is carried out preferably at a temperature of 20 to 40° C., and more preferably 25 to 35° C. for preferably 0.5 to 1.5 h, and more preferably 1 h.

According to the invention, after the seventh reaction is complete, the resultant product from the seventh reaction is dried preferably by removing the solvent through rotary evaporation to obtain a crude product of the seventh compound, and the crude product is further purified to obtain the pure seventh compound. The method for removing the solvent through rotary evaporation in the step d) is not particularly limited in the invention and may be technical solutions for removing the solvent through rotary evaporation well known by those skilled in the art. According to the invention, the crude product of the seventh compound is preferably purified using silica gel column; in the invention, the eluent employed during the process of the silica gel column purification in the step d) is preferably petroleum ether and dichloromethane, more preferably petroleum ether and dichloromethane at a mass ratio of 1:(0.5-1.5), and most preferably petroleum ether and dichloromethane at a mass ratio of 1:1.

According to the invention, after the seventh compound is obtained, the eighth reaction between the seventh compound and a metal salt compound occurs in a solvent to obtain the eighth compound having the structure represented by Formula (8). In the invention, the M and X are the same as those in the technical solutions described above and the details thereof are omitted here.

According to the invention, preferably, the seventh compound is added to the solvent, and then the resultant solution of the seventh compound and the metal salt compound are subjected to the eighth reaction to obtain the eighth compound having the structure represented by Formula (8); and more preferably, the metal salt compound is added to the solution of the seventh compound described above to carry out the eighth reaction, resulting in the eighth compound having the structure represented by Formula (8).

In the invention, the selection of the metal salt compound as well as the reaction process of the seventh compound and the metal salt compound will be influenced by the choices of M and X. In the invention, when M is Al element and X is —Cl, the metal salt compound is preferably diethyl aluminum chloride; the solvent is preferably dichloromethane, and more preferably dry dichloromethane; a mass ratio of the seventh compound, the metal salt compound and the solvent is preferably 1:(0.1-2):(24-30), more preferably 1:(0.13-0.18):(26-29), and most preferably 1:0.16:28; in the invention, preferably, the seventh compound obtained in the technical solution described above is dissolved to obtain a solution of the seventh compound, and the metal salt compound is then added to the solution of the seventh compound in an ice bath to carry out the eighth reaction, resulting in the eighth compound wherein M is Al element and X is —Cl; in the invention, the eighth reaction for preparing the eighth compound wherein M is Al element and X is —Cl is carried out preferably at a temperature of 20 to 40° C., and more preferably 25 to 35° C. for preferably 0.5 to 1.5 h, and more preferably 1 h.

In the invention, when M is Fe element and X is —Cl, the metal salt compound is preferably $FeCl_3$; the solvent is preferably dimethyl formamide (DMF), and more preferably dry DMF; a mass ratio of the seventh compound, the metal salt compound and the solvent is preferably 1:(0.2-0.5):(30-60), more preferably 1:(0.3-0.4):(40-50), and most preferably 1:0.33:48; in the invention, preferably, the seventh compound obtained in the technical solution described above is dissolved to obtain a solution of the seventh compound, and the metal salt compound is then added to and mixed with the solution of the seventh compound, which mixture is then subjected to heating under reflux condensation to carry out the eighth reaction, resulting in the eighth compound wherein M is Fe element and X is —Cl. In the invention, the duration of the heating under reflux condensation is preferably 10 to 14 h, more preferably 11 to 13 h, and most preferably 12 h.

In the invention, when X is —NO$_3$, CH$_3$COO—, CCl$_3$COO—, CF$_3$COO—, ClO$_4$—, BF$_4$—, BPh$_4$-, —CN, —N$_3$, p-methyl benzoate, p-methyl benzenesulfonate, o-nitrophenolate anion, p-nitrophenolate anion, m-nitrophenolate anion, 2,4-dinitrophenolate anion, 3,5-dinitrophenolate anion, 2,4,6-trinitrophenolate anion, 3,5-dichlorophenolate anion, 3,5-difluorophenolate anion, 3,5-bis(trifluoromethyl) phenolate anion or pentafluorophenolate anion and M is Al element or Fe element, the obtained eighth compound wherein M is Al element and X is —Cl or the obtained eighth compound wherein M is Fe element and X is —Cl and corresponding anions are subjected to a substitution reaction to obtain the eighth compound having the structure represented by Formula (8) in the invention. The method for the substitution is not particularly limited in the invention and may be carried out using the method for replacing —Cl well known by those skilled in the art in any of the step e) to step f) in the technical solution described above.

In the invention, when X is —NO$_3$ or BF$_4$, the substitution agent in the substitution reaction is preferably AgBF$_4$ or AgNO$_3$; the solvent in the substitution reaction is preferably ethanol and acetone, more preferably ethanol and acetone at a mass ratio of 1:1, and most preferably dry ethanol and acetone at a mass ratio of 1:1; a mass ratio of the eighth compound wherein M is Al element and X is —Cl or the eighth compound wherein M is Fe element and X is —Cl, the solvent and the substitution agent is preferably 1:(5-15): (0.4-0.7), more preferably 1:(8-12):(0.5-0.6), and most preferably 1:11:0.58; the duration of the substitution reaction is preferably 8 to 15 h, more preferably 10 to 13 h, and most preferably 12 h; and the substitution reaction is preferably carried out in dark.

According to the invention, after the eighth reaction is complete, preferably, the solvent is removed from the resultant reaction solution to obtain a crude product of the eighth compound, and the crude product is then purified to obtain the pure eighth compound. In the invention, the processes for removing the solvent in the eighth reaction solution and for purifying the crude product of the eighth compound vary as X varies, and are preferably specified as follows:

in the invention, when X is —Cl, the solvent is preferably removed using rotary evaporation or vacuum drying process to obtain a crude product of the eighth compound wherein X is —Cl, and the method for removing the solvent by the rotary evaporation or vacuum drying is not particularly limited in the invention and may use technical solutions for removing the solvent by rotary evaporation or vacuum drying well known by those skilled in the art; preferably, the crude product of the eighth compound is purified using silica gel column in the invention; and the eluent employed during the process of the silica gel column purification is preferably dichloromethane and methanol, more preferably dichloromethane and methanol at a mass ratio of (8-12):1, and most preferably dichloromethane and methanol at a mass ratio of 10:1.

According to the invention, when X is other substituents than —Cl in the technical solution described above, after the substitution reaction is complete, preferably, the resultant reaction solution is dried by removing the solvent through rotary evaporation, then dissolved and filtered, and finally the solvent is vacuum dried from the product after filtration to obtain the pure eighth compound wherein X is other substituent than —Cl. In the invention, the solvent is preferably dichloromethane; the methods for removing the solvent through rotary evaporation, dissolving, filtering and removing the solvent through vacuum drying are not particularly limited in the invention and may use technical solutions for removing the solvent through rotary evaporation, dissolving, filtering and removing the solvent through vacuum drying well known by those skilled in the art.

According to the invention, after the eighth compound is obtained, the eighth compound and a tertiary amine compound are subjected to the ninth reaction in a solvent, or the eighth compound and a tertiary phosphine compound are subjected to the tenth reaction in a solvent, to obtain the metalporphyrin complex having the structure represented by Formula (I). In the invention, the L is the same as that in the technical solution described above and the details thereof are omitted here. In the invention, the tertiary amine compound is preferably one of trimethylamine, tributylamine and trihexylamine; and the tertiary phosphine compound is preferably triphenylphosphine. In the invention, the solvent in the step f) is preferably tetrahydrofuran and acetonitrile, more preferably tetrahydrofuran and acetonitrile at a mass ratio of 1:1, and most preferably dry tetrahydrofuran and acetonitrile at a mass ratio of 1:1; the molar ratio of the eighth compound, the tertiary amine compound and the solvent is preferably 1:(30-45):(120-160), more preferably 1:(35-42):(125-150), and most preferably 1:40:140; and the molar ratio of the eighth compound, the tertiary phosphine compound and the solvent is preferably 1:(30-45):(120-160), more preferably 1:(35-42):(125-150), and most preferably 1:40:140;

According to the invention, preferably, the eighth compound and the tertiary amine compound are added to and mixed in a solvent, which mixture is subjected to reflux condensation to carry out the ninth reaction, resulting in the metalporphyrin complex having the structure represented by Formula (I); or preferably, the eighth compound and the tertiary phosphine compound are added to and mixed in a solvent, which mixture is subjected to reflux condensation to carry out the tenth reaction, resulting in the metalporphyrin complex having the structure represented by Formula (I). In the invention, the duration of the reflux condensation is preferably from 46 to 50 h, more preferably from 47 to 49 h, and most preferably 48 h.

According to the invention, after the ninth reaction or tenth reaction is complete, the resultant ninth reaction solution or tenth reaction solution is dried by removing the solvent through rotary evaporation to obtain the metalporphyrin complex having the structure represented by Formula (I). The method for removing the solvent through rotary evaporation in the step f) is not particularly limited in the invention and may use technical solutions for removing the solvent through rotary evaporation well known by those skilled in the art.

According to the invention, after the metalporphyrin complex is obtained, preferably, the metalporphyrin complex is vacuum dried and then stored, more preferably the metal porphyrin complex is vacuum dried in an ampoule bottle and then stored in a glovebox, and most preferably is vacuum dried by using a vacuum pump. In the invention, the vacuum drying is carried out preferably at a temperature of 40 to 60° C., more preferably 45 to 55° C., and most preferably 50° C. for preferably 10 to 14 h, more preferably 11 to 13 h, and most preferably 12 h. In the invention, gas replacement is preferably carried out using argon of high purity every 20-40 min, more preferably every 25-35 min and most preferably every 30 min during the process of vacuum drying.

In the invention, the obtained metalporphyrin complex is characterized by using the method of mass spectrum analysis and the experimental results show that the metalporphyrin complex provided according to the invention has the structure represented by Formula (I).

The invention provides a method for preparing a polycarbonate, including the steps of:

subjecting carbon dioxide and an epoxy compound to a polymerization reaction under an action of a catalyst to obtain the polycarbonates;

wherein the catalyst is the metalporphyrin complex in the technical solutions described above or the metalporphyrin complex prepared by the method in the technical solutions described above.

According to the invention, preferably, carbon dioxide, an epoxy compound and a catalyst are subjected to polymerization reaction in an autoclave to obtain the polycarbonate; more preferably, after the autoclave is baked in an oven at 70-100° C. for 2-5 h and then transferred to an glovebox and placed for 2-5 h, the catalyst and the epoxy compound are added to the autoclave in a glovebox, subsequently the autoclave is taken out of the glovebox, then carbon dioxide gas is charged into the autoclave to carry out the polymerization reaction, resulting in the polycarbonate; and most preferably, carbon dioxide gas is charged into the autoclave before the autoclave is placed into an oil bath with a preset temperature, and after 4-6 min the autoclave is adjusted to reach a preset pressure such that the polymerization reaction is carried out to obtain the polycarbonate.

In the invention, the epoxy compound is preferably one or more selected from the group consisting of ethylene oxide, propylene oxide, 1-butylene oxide, 2-butylene oxide, epoxycyclohexane, epoxycyclopentane, epoxy chloropropane, glycidyl methacrylate, methyl glycidyl ether, phenyl glycidyl ether, furfuryl glycidyl ether and styrene epoxyalkane; more preferably one or more selected from the group consisting of propylene oxide, epoxycyclohexane, epoxychloropropane, glycidyl methacrylate, furfuryl glycidyl ether and styrene epoxyalkane; and most preferably one or more of propylene oxide, epoxycyclohexane, epoxychloropropane, furfuryl glycidyl ether and styrene oxide; further, the carbon dioxide preferably has a purity of 99.99%. The metalporphyrin complex provided according to the invention has dual active centers, and it can therefore exhibit a higher catalytic activity in a smaller amount. In the invention, the molar ratio of the catalyst to the epoxy compound is preferably 1:(2500-100000), more preferably 1:(3000-15000), and most preferably 1:(5000-10000); and the pressure of the polymerization reaction is preferably 0.1 to 5 MPa, more preferably 2 to 4.5 MPa, and most preferably 3 to 4 MPa.

In the invention, the polymerization reaction is carried out preferably at a temperature of 0 to 120° C., more preferably 50 to 90° C., and most preferably 70 to 85° C. for preferably 0.5 to 48 h, more preferably 1 to 24 h, and most preferably 2 to 5 h.

According to the invention, after the polymerization reaction is complete, preferably, the obtained polymerization reaction product is cooled to 20-40° C., and unreacted carbon dioxide and unreacted epoxy compound are removed at 20-40° C.; and more preferably, the polymerization reaction product is cooled to 25-35° C. in the invention, the unreacted carbon dioxide is discharged at 25-35° C., and the unreacted epoxy compound is evacuated in a vacuum drying box.

The metalporphyrin complex provided according to the invention is employed as a catalyst for catalyzing the polymerization reaction between carbon dioxide and the epoxy compound to obtain a polycarbonate, and the catalytic activity of the catalyst is characterized by the turnover frequency (TOF) of the metalporphyrin complex catalytic system in the invention. In the invention, the method for calculating the TOF is as follows:

TOF=number of moles of the produced polycarbonate÷number of moles of the catalyst÷reaction time.

According to the invention, after the polycarbonate is obtained, the mass of the obtained polycarbonate is determined. The number of moles of the produced polycarbonate is calculated based on the mass of the polycarbonate, and thus TOF of the metalporphyrin complex catalytic system is calculated. Meanwhile, the number average molecular weight and molecular weight distribution of the polycarbonate are measured using gel permeation chromatography (GPC), and the proton nuclear magnetic resonance spectrum ($^1$H-NMR) of the polycarbonate is analyzed.

The experimental results indicate that the metalporphyrin complex catalytic system provided according to the invention has a TOF ranging from 113 $h^{-1}$ to 4610 $h^{-1}$ in catalyzing the copolymerization reaction of carbon dioxide and an epoxy compound. Meanwhile, the GPC detection results show that the polycarbonate prepared according to the invention has a number average molecular weight in a range of 37,000 to 135,000 and a molecular weight distribution in a range of 1.12 to 1.16; and the $^1$H-NMR analysis results show that in the polycarbonate prepared according to the invention, the cyclic carbonate byproduct is less than 5.0-10.0%, and the content of carbonate unit is higher than 99%.

The invention provides a metalporphyrin complex having the structure represented by formula (I), wherein $R_1$, $R_2$, $R_3$, $R_4$, $R_5$, $R_6$, $R_7$, $R_8$, $R_9$ and $R_{10}$ are independently one selected from the group consisting of hydrogen, halogen, an aliphatic group, a substituted heteroaliphatic group, an aryl group and a substituted heteroaryl group; n is a degree of polymerization and ranges from 1 to 6; L is one of a quaternary ammonium functional group and a quaternary phosphonium functional group; M is a metal element; and X is one selected from the group consisting of halogen, $—NO_3$, $CH_3COO—$, $CCl_3COO—$, $CF_3COO—$, $ClO_4—$, $BF_4—$, $BPh_4$-, $—CN$, $—N_3$, p-methyl benzoate, p-methyl benzenesulfonate, o-nitrophenolate anion, p-nitrophenolate anion, m-nitrophenolate anion, 2,4-dinitrophenolate anion, 3,5-dinitrophenolate anion, 2,4,6-trinitrophenolate anion, 3,5-dichlorophenolate anion, 3,5-difluorophenolate anion, 3,5-bis(trifluoromethyl)phenolate anion and pentafluorophenolate anion. In the invention, the metalporphyrin complex comprises two quaternary ammonium functional groups or two quaternary phosphonium functional groups, and has higher catalytic activity compared with those of the prior art when catalyzing the polymerization reaction of carbon dioxide and an epoxy compound. Further, in catalyzing the polymerization reaction of carbon dioxide and the epoxy compound, the metalporphyrin complex provided according to the invention has higher product selectivity, produces less cyclic carbonate byproducts, and results in the obtained polycarbonate having a higher number average molecular weight.

The metalporphyrin complex provided according to the invention, the preparation method thereof and the method for preparing a polycarbonate are described in detail below in combination with the examples in order to give a further understanding of the invention, but it should be understood that the description serves to further explain the features and advantages of the invention only, and shall not be construed as limitation to the scope claimed in the invention.

In the following examples, the starting materials used in the process for preparing the metalporphyrin complex according to the invention are all purchased from Sigma-Aldrich Corporation.

Example 1

Step a1): in an ice bath, a first compound having a structure represented by Formula (11) and 24 g titanium tetrachloride were added to 120 mL dry dichloromethane, and then 8 g dichloromethyl methyl ether was added to the solution of the first compound within 30 min. The resultant mixed solution was subjected to a first reaction at 35° C. After the first reaction was carried out for 30 min, the resultant first reaction solution was poured into a large beaker containing ice blocks, and then the first reaction solution was extracted using dichloromethane. An organic phase of a first intermediate product was collected and the organic phase was washed using sodium bicarbonate solution to obtain a crude product. Subsequently, the crude product was purified with silica gel column to obtain a pure product, and the eluent employed during the process of the silica gel column purification was petroleum ether and dichloromethane at a mass ratio of 1:2;

the structure of the pure product was identified, and the pure product was a second compound having a structure represented by Formula (12); and the yield of the second compound having the structure represented by Formula (12) was 60%;

(11)

(12)

step b1): 10.8 g of the second compound having the structure represented by Formula (12) and 72 g sodium iodide were added to and mixed with 70 mL dry acetonitrile, which mixture was subjected to reflux condensation for 24 h to carry out the reaction, and 150 mL water was then added to the resultant reaction solution. Subsequently, the reaction solution was extracted with ethyl ether to obtain an organic phase of a second intermediate product, and the organic phase was further dried using anhydrous magnesium sulfate to obtain a pure product;

the structure of the pure product was identified, and the pure product was the second compound having a structure represented by Formula (13); and the yield of the second compound having the structure represented by Formula (13) was 98%;

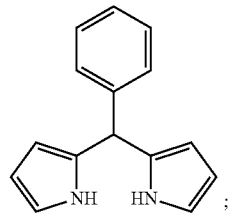
(13)

step c1): 2.12 g benzaldehyde was added to 104 mL dry pyrrole, and then 0.4 g indium chloride was added to the mixed system of benzaldehyde and pyrrole to carry out a second reaction at 25° C. After the second reaction was carried out for 2 h, 8 g sodium hydroxide powder was added to the resultant second reaction solution to carry out a third reaction at 25° C. After the third reaction was carried out for 45 min, the resultant third reaction solution was filtered and then the filtrate after the filtration was dried through evaporation to obtain a crude product of the third intermediate product. The crude product was further purified using silica gel column to obtain a pure product, and the eluent employed during the process of the silica gel column purification was petroleum ether and dichloromethane at a mass ratio of 1:2;

the structure of the pure product was identified, and the pure product was a fourth compound having a structure represented by Formula (14); and the yield of the fourth compound was 75%;

![Formula 14: dipyrromethane](NH HN) (14)

step d1): 0.44 g of the second compound having the structure represented by Formula (13) and 0.50 g of the fourth compound are added to 190 mL dry dichloromethane, and then 0.37 mL trifluoroacetic acid was added to the mixed solution of the second compound and the fourth compound to carry out a sixth reaction at 25° C. After the sixth reaction was carried out for 1 h, 0.9 g DDQ was added to the resultant sixth reaction solution to carry out a seventh reaction at 25° C. After the seventh reaction was carried out for 1 h, the resultant seventh reaction solution was dried by removing the solvent through rotary evaporation to obtain a crude product of a fourth intermediate product. The crude product was further purified using silica gel column to obtain a pure product, and the eluent employed during the process of the silica gel column purification was petroleum ether and dichloromethane at a mass ratio of 1:1;

the structure of the pure product was identified, and the pure product was a seventh compound having a structure represented by Formula (15); and the yield of the seventh compound was 30%;

(15)

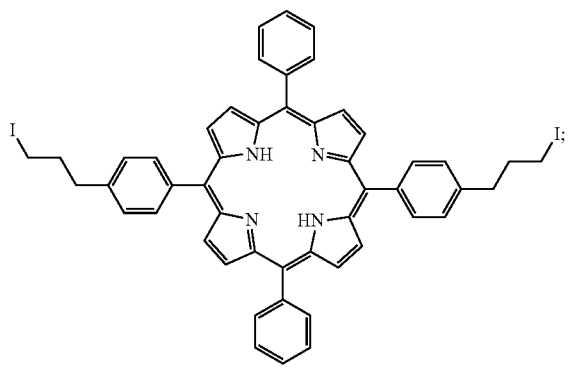

step e1): 0.95 g of the seventh compound was added to 20 mL dry dichloromethane, and 0.16 mL diethyl aluminum chloride was added to the solution of the seventh compound in an ice bath. The resultant mixed solution was subjected to an eighth reaction at 25° C. After the eighth reaction was carried out for 1 h, the resultant eighth reaction solution was dried by removing the solvent through rotary evaporation to obtain a crude product of a fifth intermediate product. The crude product was further purified using silica gel column to obtain a pure product, and the eluent employed during the process of the silica gel column purification was dichloromethane and methanol at a mass ratio of 10:1;

the structure of the pure product was identified, and the pure product was an eighth compound having a structure represented by Formula (16); and the yield of the eighth compound was 95%;

(16)

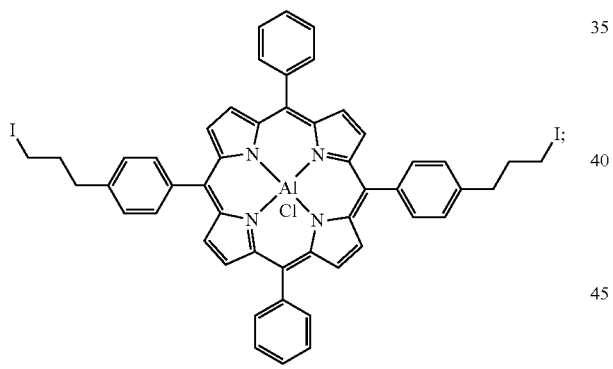

and step f1): 1.0 g of the eighth compound and 7.4 g tributylamine were added to and mixed with 10 mL of dry mixed solvent of tetrahydrofuran and acetonitrile, which mixture was subjected to reflux condensation for 48 h to carry out a ninth reaction, and then the resultant ninth reaction solution was dried by removing the solvent through rotary evaporation to obtain a metalporphyrin complex. A mass ratio of tetrahydrofuran to acetonitrile in the mixed solvent was 1:1; and the yield of the metalporphyrin complex was 98%.

In the invention, after the metalporphyrin complex was prepared, the obtained metalporphyrin complex was put into an ampoule bottle for evacuation treatment. A vacuum pump was used for successive evacuation at 50° C. for 12 h, and gas replacement was carried out with argon of high purity every 30 min during the process of evacuation. The metalporphyrin complex after vacuum drying was stored in a glovebox.

In the invention, the prepared metalporphyrin complex was analyzed using mass spectrum. The results of the mass spectrum test show that [Example 1-I$^-$] has a molecular weight of 1253, and [IV-I$^-$] has a molecular weight of 1252.5 according to theoretical calculation based on the structure represented by Formula (IV). Therefore, the metalporphyrin complex prepared in this example has the structure represented by Formula (IV).

Example 2

Step a2): in an ice bath, 18 g of a first compound having a structure represented by Formula (17) and 24 g titanium tetrachloride were added to 120 mL dry dichloromethane, and then 8 g dichloromethyl methyl ether was added to the solution of the first compound within 30 min. The resultant mixed solution was subjected to a first reaction at 35° C. After the first reaction was carried out for 30 min, the resultant first reaction solution was poured into a large beaker containing ice blocks, and then the first reaction solution was extracted using dichloromethane. An organic phase of a first intermediate product was collected and the organic phase was washed using sodium bicarbonate solution to obtain a crude product. Subsequently, the crude product was purified with silica gel column to obtain a pure product, and the eluent employed during the process of the silica gel column purification was petroleum ether and dichloromethane at a mass ratio of 1:2;

the structure of the pure product was identified, and the pure product was a second compound having a structure represented by Formula (18); and the yield of the second compound having the structure represented by Formula (18) was 60%;

(17)

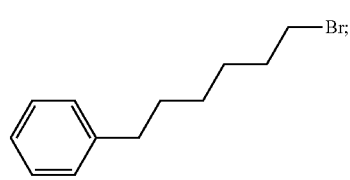

(18)

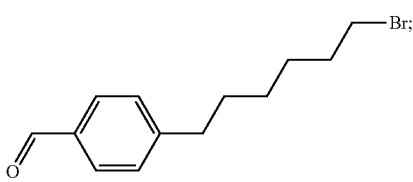

step b2): 12.5 g of the second compound having the structure represented by Formula (18) and 72 g sodium iodide were added to and mixed with 70 mL dry acetonitrile, which mixture was subjected to reflux condensation for 24 h to carry out the reaction, and 150 mL water was then added to the resultant reaction solution. Subsequently, the solution was extracted with ethyl ether to obtain an organic phase of a second intermediate product, and the organic phase was further dried using anhydrous magnesium sulfate to obtain a pure product;

the structure of the pure product was identified, and the pure product was the second compound having a structure represented by Formula (19); and the yield of the second compound having the structure represented by Formula (19) was 98%;

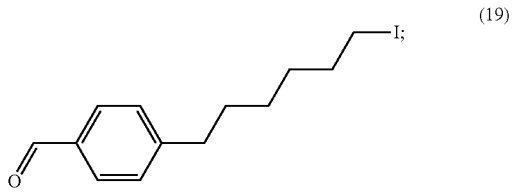 [SMILES: O=Cc1ccc(CCCCCCI)cc1]

(19)

step c2): 3.92 g pentafluorobenzaldehyde was added to 104 mL dry pyrrole, and then 0.4 g indium chloride was added to the solution of pentafluorobenzaldehyde to carry out a second reaction at 25° C. After the second reaction was carried out for 2 h, 8 g sodium hydroxide powder was added to the resultant second reaction solution to carry out a third reaction at 25° C. After the third reaction was carried out for 45 min, the resultant third reaction solution was filtered and then the filtrate after the filtration was dried through evaporation to obtain a crude product of a third intermediate product. The crude product was further purified using silica gel column to obtain a pure product, and the eluent employed during the process of the silica gel column purification was petroleum ether and dichloromethane at a mass ratio of 1:2;

the structure of the pure product was identified, and the pure product was a fourth compound having a structure represented by Formula (20); and the yield of the fourth compound was 75%;

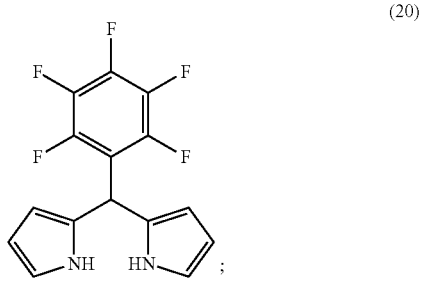 [SMILES: Fc1c(F)c(F)c(C(c2ccc[nH]2)c2ccc[nH]2)c(F)c1F]

(20)

step d2): 0.63 g of the second compound having the structure represented by Formula (19) and 0.62 g of the fourth compound were added to 190 mL dry dichloromethane, and then 0.37 mL trifluoroacetic acid was added to a mixed solution of the second compound and the fourth compound to carry out a sixth reaction at 25° C. After the sixth reaction was carried out for 1 h, 0.9 g DDQ was added to the resultant sixth reaction solution to carry out a seventh reaction at 25° C. After the seventh reaction was carried out for 1 h, the resultant seventh reaction solution was dried by removing the solvent through rotary evaporation to obtain a crude product of a fourth intermediate product. The crude product was further purified using silica gel column to obtain a pure product, and the eluent employed during the process of the silica gel column purification was petroleum ether and dichloromethane at a mass ratio of 1:1;

the structure of the pure product was identified, and the pure product was a seventh compound having a structure represented by Formula (21); and the yield of the seventh compound was 30%;

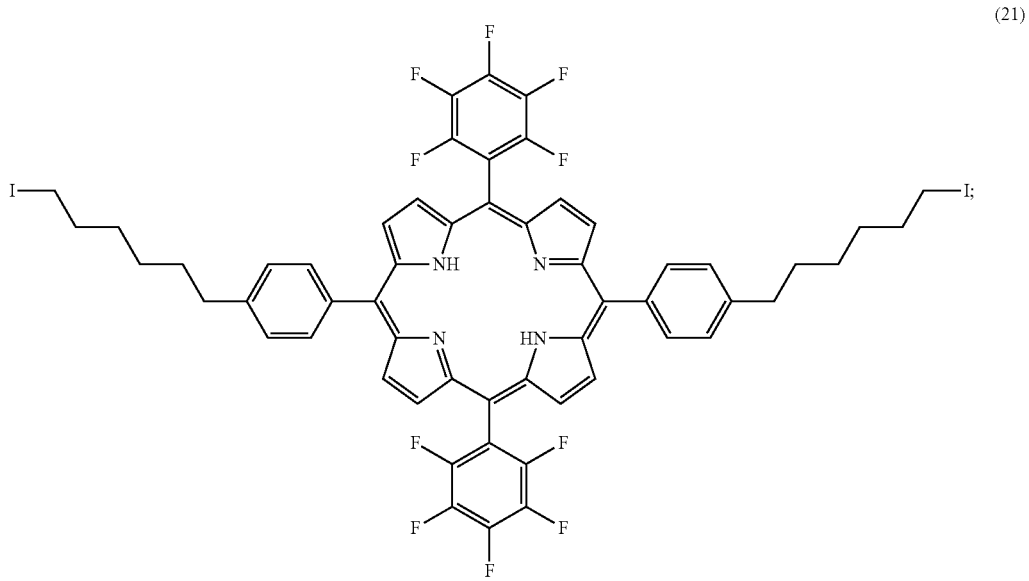 [SMILES: Fc1c(F)c(F)c(-c2c3nc(c(-c4ccc(CCCCCCI)cc4)c4ccc([nH]4)c(-c4c(F)c(F)c(F)c(F)c4F)c4nc(c(-c5ccc(CCCCCCI)cc5)c5ccc2[nH]5)C=C4)C=C3)c(F)c1F]

(21)

step e2): 1.21 g of the seventh compound was added to 20 mL dry dichloromethane, and 0.16 mL diethyl aluminum chloride was added to the solution of the seventh compound in an ice bath. The resultant mixed solution was subjected to an eighth reaction at 25° C. After the eighth reaction was carried out for 1 h, the resultant eighth reaction solution was dried by removing the solvent through rotary evaporation to obtain a crude product of a fifth intermediate product. The crude product was further purified using silica gel column to obtain a pure product, and the eluent employed during the process of the silica gel column purification was dichloromethane and methanol at a mass ratio of 10:1;

the structure of the pure product was identified, and the pure product was an eighth compound having a structure represented by Formula (22); and the yield of the eighth compound was 95%;

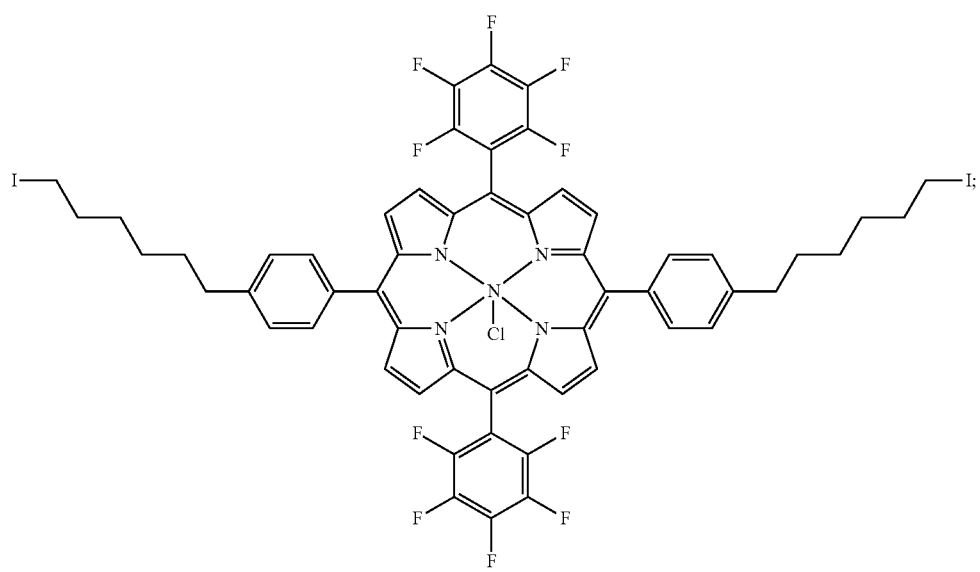

(22)

and step f2): 1.27 g of the eighth compound and 2.3 g trimethylamine were added to and mixed with 10 mL of dry mixed solvent of tetrahydrofuran and acetonitrile, which mixture was subjected to reflux condensation for 48 h to carry out a ninth reaction, and then the resultant ninth reaction solution was dried by removing the solvent through rotary evaporation to obtain a metalporphyrin complex. A mass ratio of tetrahydrofuran to acetonitrile in the mixed solvent was 1:1; and the yield of the metalporphyrin complex was 98%.

In the invention, after the metalporphyrin complex was prepared, the obtained metalporphyrin complex was stored after being vacuum dried according to the technical solution described in Example 1.

In the invention, the prepared metalporphyrin complex was analyzed using mass spectrum. The results of the mass spectrum test show that [Example 2-I$^-$] has a molecular weight of 1265, and [V-I$^-$] has a molecular weight of 1265 according to theoretical calculation based on the structure represented by Formula (V). Therefore, the metalporphyrin complex prepared in this example has a structure represented by Formula (V).

Example 3

Step a3): the second compound having the structure represented by Formula (13) was prepared according to the methods described in step a1) to step b1) of Example 1;

step b3): 2.40 g p-methyl benzaldehyde was added to 104 mL dry pyrrole, and then 0.4 g indium chloride was added to the solution of p-methyl benzaldehyde to carry out a second reaction at 25° C. After the second reaction was carried out for 2 h, 8 g sodium hydroxide powder was added to the resultant second reaction solution to carry out a third reaction at 25° C. After the third reaction was carried out for 45 min, the resultant third reaction solution was filtered and then the filtrate after the filtration was dried through evaporation to obtain a crude product of a first intermediate product. The crude product was further purified using silica gel column to obtain a pure product, and the eluent employed during the process of the silica gel column purification was petroleum ether and dichloromethane at a mass ratio of 1:2;

the structure of the pure product was identified, and the pure product was a fourth compound having a structure represented by Formula (23); and the yield of the fourth compound was 75%;

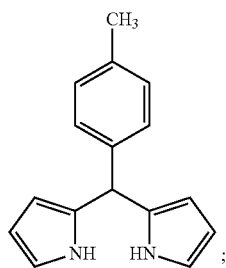

(23)

step c3): 0.44 g of the second compound having the structure represented by Formula (13) and 0.44 g of the fourth compound were added to 190 mL dry dichloromethane, and then 0.37 mL trifluoroacetic acid was added to a mixed solution of the second compound and the fourth compound to carry out the sixth reaction at 25° C. After the sixth reaction was carried out for 1 h, 0.9 g DDQ was added to the resultant sixth reaction solution to carry out a seventh reaction at 25° C. After the seventh reaction was carried out for 1 h, the resultant seventh reaction solution was dried by removing the solvent through rotary evaporation to obtain a crude product of a second intermediate product. The crude product was further purified using silica gel column to obtain a pure product, and the eluent employed during the process of the silica gel column purification was petroleum ether and dichloromethane at a mass ratio of 1:1;

the structure of the pure product was identified, and the pure product was a seventh compound having a structure represented by Formula (24); and the yield of the seventh compound was 30%;

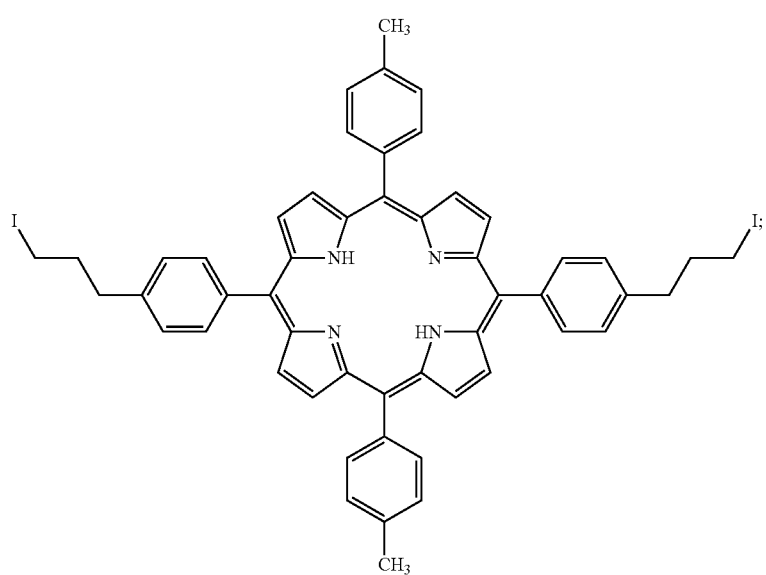

(24)

step d3): 0.98 g of the seventh compound was added to 20 mL dry dichloromethane, and 0.16 mL diethyl aluminum chloride was added to the solution of the seventh compound in an ice bath. The resultant mixed solution was subjected to an eighth reaction at 25° C. After the eighth reaction was carried out for 1 h, the resultant eighth reaction solution was dried by removing the solvent through rotary evaporation to obtain a crude product of a third intermediate product. The crude product was further purified using silica gel column to obtain a pure product, and the eluent employed during the process of the silica gel column purification was dichloromethane and methanol at a mass ratio of 10:1;

the structure of the pure product was identified, and the pure product was an eighth compound having a structure represented by Formula (25); and the yield of the eighth compound was 95%;

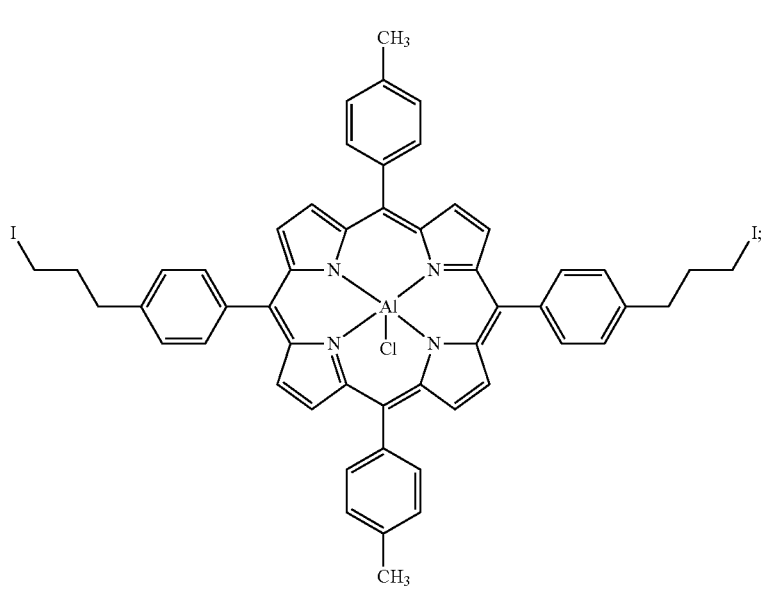

(25)

and step e3): 1.04 g of the eighth compound and 10.8 g trihexylamine were added to and mixed with 10 mL of dry mixed solvent of tetrahydrofuran and acetonitrile, which mixture was subjected to reflux condensation for 48 h to carry out a ninth reaction, and then the resultant ninth reaction solution was dried by removing the solvent through rotary evaporation to obtain a metalporphyrin complex. A mass ratio of tetrahydrofuran to acetonitrile in the mixed solvent was 1:1; and the yield of the metalporphyrin complex was 98%.

In the invention, after the metalporphyrin complex was prepared, the obtained metalporphyrin complex was stored after being vacuum dried according to the technical solution described in Example 1.

In the invention, the prepared metalporphyrin complex was analyzed using mass spectrum. The results of the mass spectrum test show that [Example 3-I⁻] has a molecular weight of 1450, and [VI-I⁻] has a molecular weight of 1450 according to theoretical calculation based on the structure represented by Formula (VI). Therefore, the metal porphyrin complex prepared in this example has the structure represented by Formula (VI).

Example 4

Step a4): in an ice bath, 14 g of a first compound having a structure represented by Formula (26) and 24 g titanium tetrachloride were added to 120 mL dry dichloromethane, and then 8 g dichloromethyl methyl ether was added to the solution of the first compound within 30 min. The resultant mixed solution was subjected to a first reaction at 35° C. After the first reaction was carried out for 30 min, the resultant first reaction solution was poured into a large beaker containing ice blocks, and then the first reaction solution was extracted using dichloromethane. An organic phase of a first intermediate product was collected and the organic phase was washed using sodium bicarbonate solution to obtain a crude product Subsequently, the crude product was purified with silica gel column to obtain a pure product, and the eluent employed during the process of the silica gel column purification was petroleum ether and dichloromethane at a mass ratio of 1:2;

the structure of the pure product was identified, and the pure product was a second compound having a structure represented by Formula (27); and the yield of the second compound having the structure represented b Formula (27) was 60%;

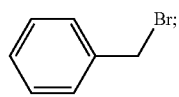  (26)

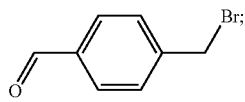  (27)

step b4): 9.6 g of the second compound having the structure represented by Formula (27) and 72 g sodium iodide were added to and mixed with 70 mL dry acetonitrile, which mixture was subjected to reflux condensation for 24 h to carry out the reaction, and 150 mL water was then added to the resultant reaction solution. Subsequently, the solution was extracted with ethyl ether to obtain an organic phase of a second intermediate product, and the organic phase was further dried using anhydrous magnesium sulfate to obtain a pure product;

the structure of the pure product was identified, and the pure product was the second compound having a structure represented by Formula (28); and the yield of the second compound having the structure represented by Formula (28) was 98%;

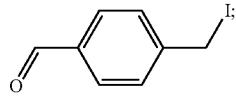  (28)

step c4): 3.0 g p-ethoxy benzaldehyde was added to 104 mL dry pyrrole, and then 0.4 g indium chloride was added to the solution of p-ethoxy benzaldehyde to carry out a second reaction at 25° C. After the second reaction was carried out for 2 h, 8 g sodium hydroxide powder was added to the resultant second reaction solution to carry out a third reaction at 25° C. After the third reaction was carried out for 45 min, the resultant third reaction solution was filtered and then the filtrate after the filtration was dried through evaporation to obtain a crude product of a third intermediate product. The crude product was further purified using silica gel column to obtain a pure product, and the eluent employed during the process of the silica gel column purification was petroleum ether and dichloromethane at a mass ratio of 1:2;

the structure of the pure product was identified, and the pure product was a fourth compound having a structure represented by Formula (29); and the yield of the fourth compound was 75%;

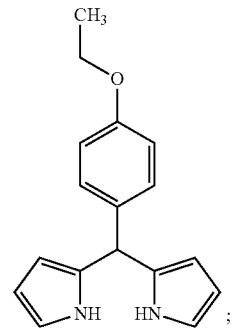  (29)

and step d4): 0.49 g of the second compound having the structure represented by Formula (28) and 0.53 g of the fourth compound are added to 190 mL dry dichloromethane, and then 0.37 mL trifluoroacetic acid was added to a mixed solution of the second compound and the fourth compound to carry out a sixth reaction at 25° C. After the sixth reaction was carried out for 1 h, 0.9 g DDQ was added to the resultant sixth reaction solution to carry out a seventh reaction at 25° C. After the seventh reaction was carried out for 1 h, the resultant seventh reaction solution was dried by removing the solvent through rotary evaporation to obtain a crude product of a fourth intermediate product. The crude product was further purified using silica gel column to obtain a pure product, and the eluent employed during the process of the silica gel column purification was petroleum ether and dichloromethane at a mass ratio of 1:1;

the structure of the pure product was identified, and the pure product was a seventh compound having a structure represented by Formula (30); and the yield of the seventh compound was 30%;

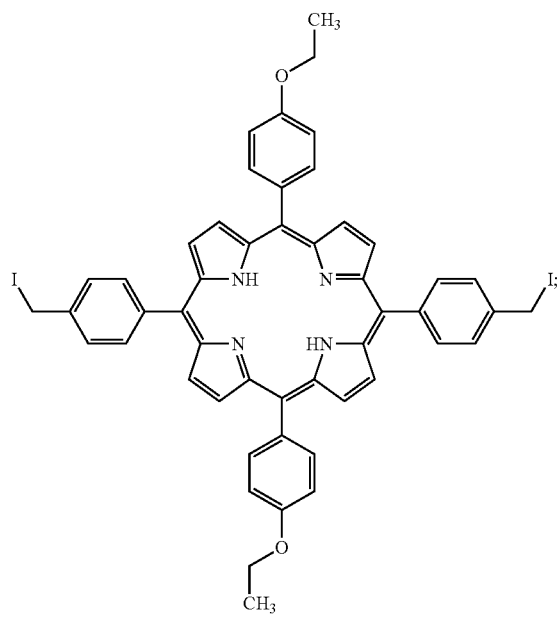

(30)

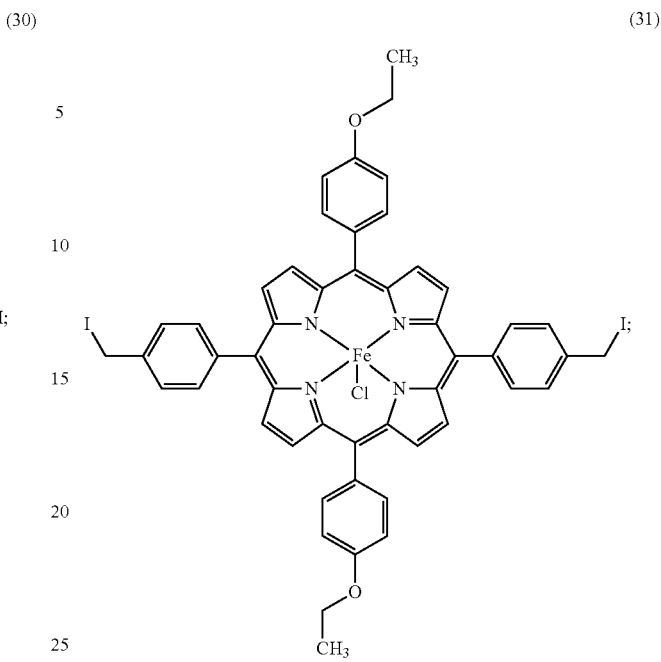

(31)

step e4): 0.98 g of the seventh compound was added to 50 mL dry DMF, and then 0.33 g FeCl$_3$ was added to and mixed with the solution of the seventh compound, which mixture was subjected to heating under reflux condensation for 12 h to carry out an eighth reaction, resulting in a crude product of a fifth intermediate product. The crude product was further purified using silica gel column to obtain a pure product, and the eluent employed during the process of the silica gel column purification was dichloromethane and methanol at a mass ratio of 10:1;

the structure of the pure product was identified, and the pure product was an eighth compound having a structure represented by Formula (31); and the yield of the eighth compound was 95%;

step f4): 1.07 g of the eighth compound and 7.4 g tributylamine were added to and mixed with 10 mL of dry mixed solvent of tetrahydrofuran and acetonitrile, which mixture was subjected to reflux condensation for 48 h to carry out a ninth reaction, and then the resultant ninth reaction solution was dried by removing the solvent through rotary evaporation to obtain a sixth intermediate product. A mass ratio of tetrahydrofuran to acetonitrile in the mixed solvent was 1:1;

the structure of the sixth intermediate product was identified, and the sixth intermediate product was a compound having a structure represented by Formula (32); and the yield of the compound having the structure represented by Formula (32) was 98%;

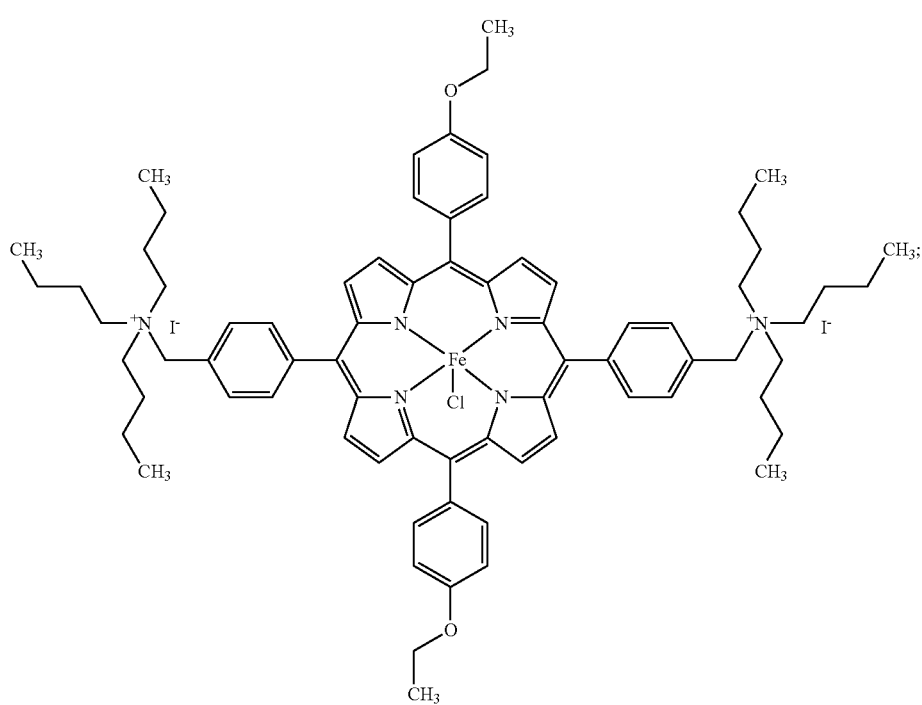

(32)

and step g4): 1.47 g of the compound having the structure represented by Formula (32) was dissolved in 20 mL of dry mixed solvent of ethanol and acetone, and a mass ratio of ethanol to acetone in the mixed solvent was 1:1. Then, 0.85 g $AgBF_4$ was added to the solution of the compound to react in the dark for 12 h. The resultant reaction solution was dried by removing the solvent through rotary evaporation before dissolving in dichloromethane, and the resultant product after dissolution was filtered. Finally, the product after filtration was vacuum dried by removing dichloromethane to obtain a metalporphyrin complex; and the yield of the metalporphyrin complex was 98%.

In the invention, after the metalporphyrin complex was prepared, the obtained metalporphyrin complex was stored after being vacuum dried according to the technical solution described in Example 1.

In the invention, the prepared metalporphyrin complex was analyzed using mass spectrum. The results of the mass spectrum test show that [Example 4-$BF_4^-$] has a molecular weight of 1359, and [VII-$BF_4^-$] has a molecular weight of 1359 according to theoretical calculation based on the structure represented by Formula (VII). Therefore, the metalporphyrin complex prepared in this example has a structure represented by Formula (VII).

Example 5

Step a5): the second compound having the structure represented by Formula (13) was prepared according to the methods described in step a1) to step b1) in Example 1;

step b5): 3.6 g p-phenyl benzaldehyde was added to 104 mL dry pyrrole, and then 0.4 g indium chloride was added to the solution of p-phenyl benzaldehyde to carry out a second reaction at 25° C. After the second reaction was carried out for 2 h, 8 g sodium hydroxide powder was added to the resultant second reaction solution to carry out a third reaction at 25° C. After the third reaction was carried out for 45 min, the resultant third reaction solution was filtered and then the filtrate after the filtration was dried through evaporation to obtain a crude product of a first intermediate product. The crude product was further purified using silica gel column to obtain a pure product, and the eluent employed during the process of the silica gel column purification was petroleum ether and dichloromethane at a mass ratio of 1:2;

the structure of the pure product was identified, and the pure product was a fourth compound having a structure represented by Formula (33); and the yield of the fourth compound was 75%;

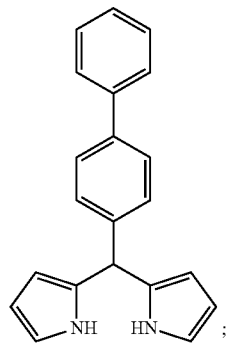

(33)

step c5): 0.44 g of the second compound having the structure represented by Formula (13) and 0.59 g of the fourth compound were added to 190 mL dry dichloromethane, and then 0.37 mL trifluoroacetic acid was added to a mixed solution of the second compound and the fourth compound to carry out a sixth reaction at 25° C. After the sixth reaction was carried out for 1 h, 0.9 g DDQ was added to the resultant sixth reaction solution to carry out a seventh reaction at 25° C. After the seventh reaction was carried out for 1 h, the resultant seventh reaction solution was dried by removing the solvent through rotary evaporation to obtain a crude product of a second intermediate product. The crude product was further purified using silica gel column to obtain a pure product, and the eluent employed during the process of the silica gel column purification was petroleum ether and dichloromethane at a mass ratio of 1:1;

the structure of the pure product was identified, and the pure product was a seventh compound having a structure represented by Formula (34); and the yield of the seventh compound was 30%;

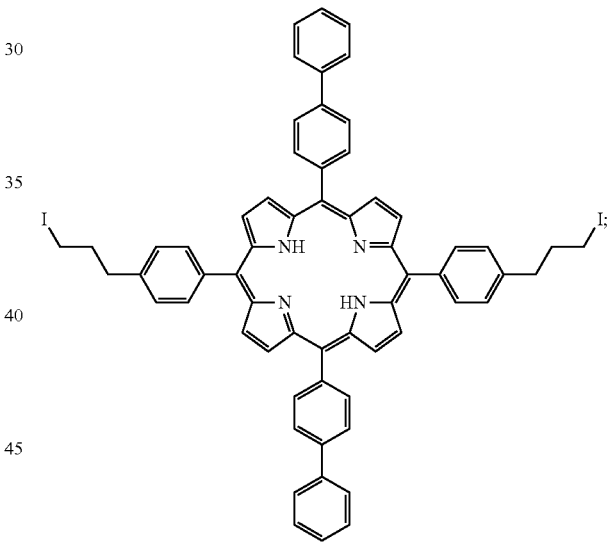

(34)

step d5): 1.10 g of the seventh compound was added to 50 mL dry DMF, and then 0.33 g $FeCl_3$ was added to and mixed with the solution of the seventh compound, which mixture was subjected to heating under reflux condensation for 12 h to carry out an eighth reaction, resulting in a crude product of a third intermediate product. The crude product was further purified using silica gel column to obtain a pure product, and the eluent employed during the process of the silica gel column purification was dichloromethane and methanol at a mass ratio of 10:1;

the structure of the pure product was identified, and the pure product was an eighth compound having a structure represented by Formula (35); and the yield of the eighth compound was 95%;

(35)

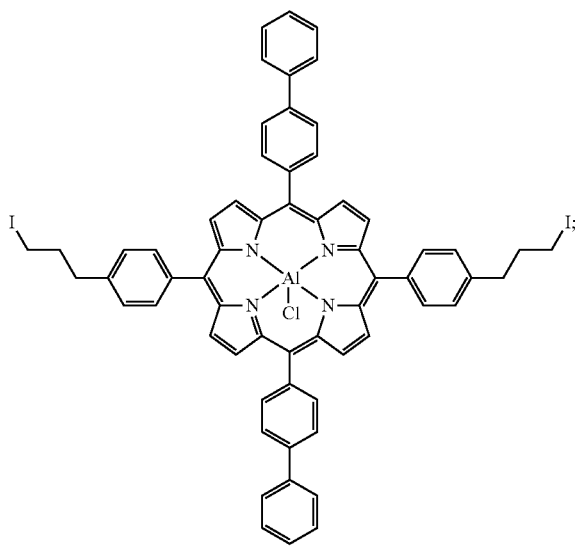

step e5): 1.13 g of the eighth compound and 7.4 g tributylamine were added to and mixed with 10 mL of dry mixed solvent of tetrahydrofuran and acetonitrile, which mixture was subjected to reflux condensation for 48 h to carry out a ninth reaction, and then the resultant ninth reaction solution was dried by removing the solvent through rotary evaporation to obtain a fourth intermediate product. A mass ratio of tetrahydrofuran to acetonitrile in the mixed solvent was 1:1;

the structure of the fourth intermediate product was identified, and the fourth intermediate product was a compound having a structure represented by Formula (36); and the yield of the compound having the structure represented by Formula (36) was 98%;

and step f5): 1.53 g of the compound having the structure represented by Formula (36) was dissolved in 20 mL of dry mixed solvent of ethanol and acetone, and a mass ratio of ethanol to acetone in the mixed solvent was 1:1. Subsequently, 0.77 g $AgNO_3$ was added to the solution of the compound to react in the dark for 12 h. The resultant reaction solution was dried by removing the solvent through rotary evaporation before dissolving in dichloromethane, and the resultant product after dissolution was filtered. Finally, the product after filtration was vacuum dried by removing dichloromethane to obtain a metalporphyrin complex; and the yield of the metalporphyrin complex was 98%.

In the invention, after the metalporphyrin complex was prepared, the obtained metalporphyrin complex was stored after being vacuum dried according to the technical solution described in Example 1.

In the invention, the prepared metalporphyrin complex was analyzed using mass spectrum. The results of the mass spectrum test show that [Example 5-$NO_3^-$] has a molecular weight of 1397, and [VIII-$NO_3^-$] has a molecular weight of 1397 according to theoretical calculation based on the structure represented by Formula (VIII). Therefore, the metalporphyrin complex prepared in this example has a structure represented by Formula (VIII).

Example 6

Step a6): the second product having the structure represented by Formula (13) was prepared according to the methods described in step a1) to step b1) of Example 1;

step b6): 4.3 g 3-chlorobiphenyl-4-benzaldehyde was added to 104 mL dry pyrrole, and then 0.4 g indium chloride was added to the solution of 3-chlorobiphenyl-4-benzalde- (36)

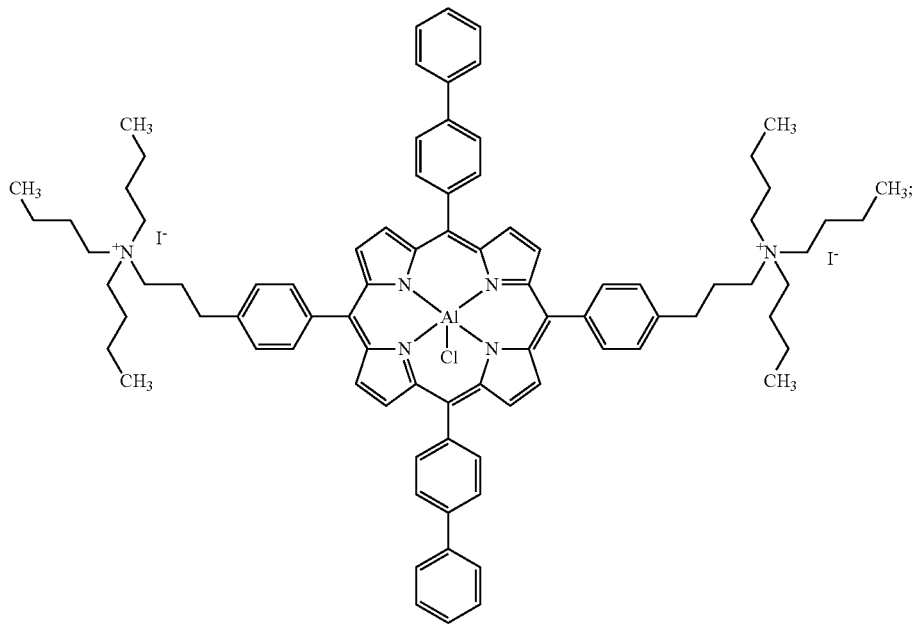

hyde to carry out a second reaction at 25° C. After the second reaction was carried out for 2 h, 8 g sodium hydroxide powder was added to the resultant second reaction solution to carry out a third reaction at 25° C. After the third reaction was carried out for 45 min, the resultant third reaction solution was filtered and then the filtrate after the filtration was dried through evaporation to obtain a crude product of a first intermediate product. The crude product was further purified using silica gel column to obtain a pure product, and the eluent employed during the process of the silica gel column purification was petroleum ether and dichloromethane at a mass ratio of 1:2;

the structure of the pure product was identified, and the pure product was a fourth compound having a structure represented by Formula (37); and the yield of the fourth compound was 75%;

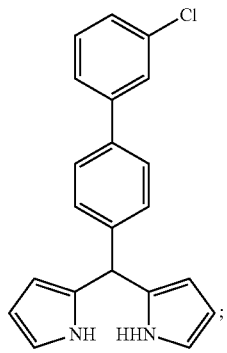

(37)

step c6): 0.44 g of the second compound having the structure represented by Formula (13) and 0.66 g of the fourth compound were added to 190 mL dry dichloromethane, and then 0.37 mL trifluoroacetic acid was added to a mixed solution of the second compound and the fourth compound to carry out a sixth reaction at 25° C. After the sixth reaction was carried out for 1 h, 0.9 g DDQ was added to the resultant sixth reaction solution to carry out a seventh reaction at 25° C. After the seventh reaction was carried out for 1 h, the resultant seventh reaction solution was dried by removing the solvent through rotary evaporation to obtain a crude product of a second intermediate product. The crude product was further purified using silica gel column to obtain a pure product, and the eluent employed during the process of the silica gel column purification was petroleum ether and dichloromethane at a mass ratio of 1:1;

the structure of the pure product was identified, and the pure product was a seventh compound having a structure represented by Formula (38); and the yield of the seventh compound was 30%;

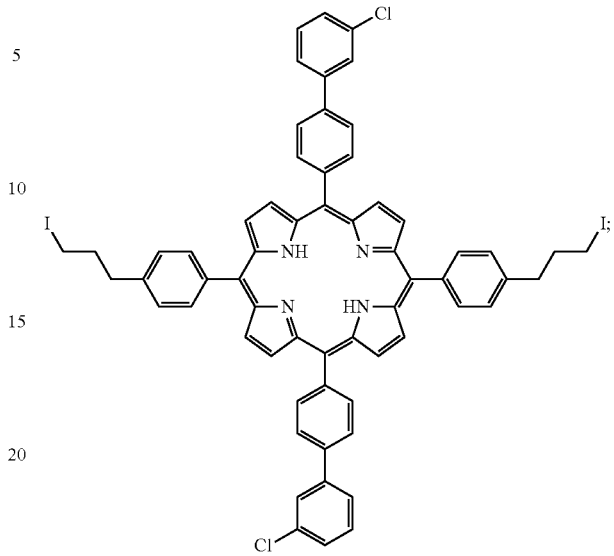

(38)

step d6): 1.17 g of the seventh compound was added to 50 mL dry DMF, and then 0.33 g FeCl₃ was added to and mixed with the solution of the seventh compound, which mixture was subjected to heating under reflux condensation for 12 h to carry out an eighth reaction, resulting in a crude product of a third intermediate product. The crude product was further purified using silica gel column to obtain a pure product, and the eluent employed during the process of the silica gel column purification was dichloromethane and methanol at a mass ratio of 10:1;

the structure of the pure product was identified, and the pure product was an eighth compound having a structure represented by Formula (39); and the yield of the eighth compound was 95%;

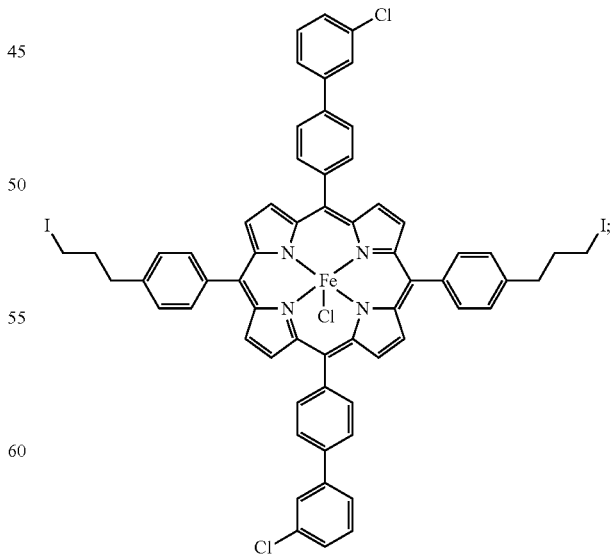

(39)

step e6): 1.23 g of the eighth compound and 7.4 g tributylamine were added to and mixed with 10 mL of dry mixed solvent of tetrahydrofuran and acetonitrile, which mixture was subjected to reflux condensation for 48 h to carry out a ninth reaction, and then the resultant ninth reaction solution was dried by removing the solvent through rotary evaporation to obtain a fourth intermediate product. A mass ratio of tetrahydrofuran to acetonitrile in the mixed solvent was 1:1;

the structure of the fourth intermediate product was identified, and the fourth intermediate product was a compound having a structure represented by Formula (40); and the yield of the compound having the structure represented by Formula (40) was 98%;

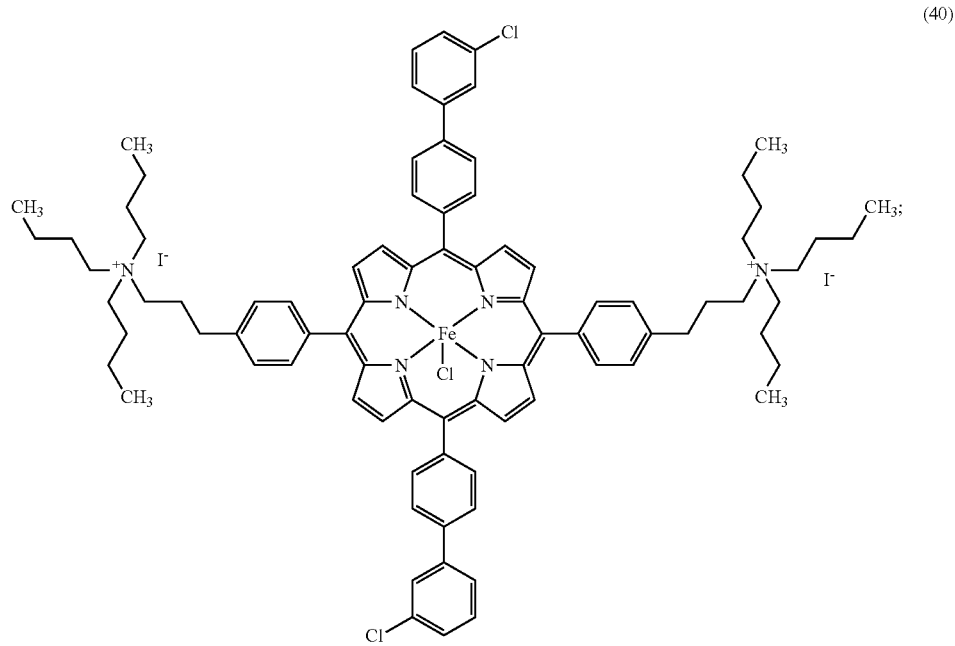

(40)

step f6): 1.60 g of the compound having the structure represented by Formula (40) was dissolved in 20 mL of dry mixed solvent of ethanol and acetone to carry out the reaction, and a mass ratio of ethanol to acetone in the mixed solvent was 1:1. Subsequently, 0.77 g AgNO$_3$ was added to the solution of the compound to react in the dark for 12 h. The resultant reaction solution was dried by removing the solvent through rotary evaporation before dissolving in dichloromethane, and then the resultant product from dissolution was filtered. Finally, the product after filtration was vacuum dried by removing dichloromethane to obtain a metalporphyrin complex; and the yield of the metalporphyrin complex was 98%.

In the invention, after the metalporphyrin complex was prepared, the obtained metalporphyrin complex was stored after being vacuum dried according to the technical solution described in Example 1.

In the invention, the prepared metalporphyrin complex was analyzed using mass spectrum. The results of the mass spectrum test show that [Example 6-NO$_3^-$] has a molecular weight of 1465, and [IX-NO$_3^-$] has a molecular weight of 1465 according to theoretical calculation based on the structure represented by Formula (IX). Therefore, the metalporphyrin complex prepared in this example has a structure represented by Formula (IX).

Example 7

Step a7), the eighth compound having the structure represented by Formula (16) was prepared according to the methods described in step a1) to step e1) of Example 1;

step b7), 1.0 g of the eighth compound having the structure represented by Formula (16) and 10.5 g triphenyl phosphine were added to and mixed with 10 mL of dry mixed solvent of tetrahydrofuran and acetonitrile, which mixture was subjected to reflux condensation for 48 h to carry out a tenth reaction. The resultant tenth reaction solution was dried by removing the solvent through rotary evaporation to obtain a metalporphyrin complex. A mass ratio of tetrahydrofuran to acetonitrile in the mixed solvent was 1:1; and the yield of the metalporphyrin complex was 98%.

In the invention, after the metalporphyrin complex was prepared, the obtained metalporphyrin complex was stored after being vacuum dried according to the technical solution described in Example 1.

In the invention, the prepared metalporphyrin complex was analyzed using mass spectrum. The results of the mass spectrum test show that [Example 7-I$^-$] has a molecular weight of 1407, and [X-I$^-$] has a molecular weight of 1407 according to theoretical calculation based on the structure represented by Formula (X). Therefore, the metalporphyrin complex prepared in this example has the structure represented by Formula (X).

Example 8

In the invention, carbon dioxide and an epoxy compound were polymerized in an autoclave, and before the polymerization reaction occurs, the autoclave was subjected to water removal and oxygen removal treatment using the following specific method:

the autoclave was subjected to pressure reduction and argon replacement treatment in a vacuum oven at 80° C., and the operations for the pressure reduction and argon replacement were repeated once per hour for a total of 3 times to achieve the purpose of removing water and oxygen from the autoclave. Then the autoclave was put into a glovebox.

In a glovebox, 0.025 mmol of the metalporphyrin complex prepared according to Example 1 and 75 mmol of dry propylene oxide were added to a 15 mL autoclave that had been subjected to water removal and oxygen removal. Then the autoclave was taken out of the glovebox and carbon dioxide was charged into the autoclave through a carbon dioxide supply line with pressure regulation function to bring the pressure in the autoclave to 0.1 MPa. A temperature of the autoclave was controlled to be 25° C. and the polymerization reaction was carried out for 5 h. After the polymerization reaction was complete, the autoclave was cooled to 25° C., the carbon dioxide in the autoclave was discharged, and the unreacted propylene oxide was evacuated in a vacuum drying box at 25° C. to obtain a polycarbonate.

In the invention, the prepared polycarbonate was weighed, and the weight of the polycarbonate was 0.7 g. The catalytic system of the metalporphyrin complex prepared according to Example 1 has a TOF of 113 $h^{-1}$ calculated based on the weight of the polycarbonate. The prepared polycarbonate has a number average molecular weight of 40000 and a molecular weight distribution of 1.14 measured with GPC. It was also subjected to a $^1$H-NMR analysis, and the analytic results show that in the prepared polycarbonate, the cyclic carbonate byproduct is less than 5%, and the carbonate unit content is higher than 99%.

Example 9

The autoclave was subjected to water removal and oxygen removal treatment according to the technical solution described in Example 8.

In a glovebox, 0.025 mmol of the metalporphyrin complex prepared according to Example 2 and 75 mmol of dry epoxycyclohexane were added to a 15 mL autoclave that had been subjected to water removal and oxygen removal treatment. Then the autoclave was taken out of the glovebox and carbon dioxide was charged into the autoclave through a carbon dioxide supply line with pressure regulation function to bring the pressure in the autoclave to 4 MPa. A temperature of the autoclave was controlled to be 25° C. and the polymerization reaction was carried out for 5 h. After the polymerization reaction was complete, the autoclave was cooled to 25° C., the carbon dioxide in the autoclave was discharged, and the unreacted epoxycyclohexane was evacuated in a vacuum drying box at 25° C. to obtain a polycarbonate.

In the invention, the prepared polycarbonate was weighed, and the weight of the polycarbonate was 2.15 g. The catalytic system of the metalporphyrin complex prepared according to Example 2 has a TOE of 680 $h^{-1}$ calculated based on the weight of the polycarbonate. The prepared polycarbonate has a number average molecular weight of 37000 and a molecular weight distribution of 1.12 measured with GPC. It was also subjected to a $^1$H-NMR analysis, and the analytic results show that in the prepared polycarbonate, the cyclic carbonate byproduct is less than 5%, and the carbonate unit content is higher than 99%.

Example 10

The autoclave was subjected to water removal and oxygen removal treatment according to the technical solution described in Example 8.

In a glovebox, 0.005 mmol of the metalporphyrin complex prepared according to Example 3 and 75 mmol of dry furfuryl glycidyl ether were added to a 15 mL autoclave that had been subjected to water removal and oxygen removal treatment. Then the autoclave was taken out of the glovebox and carbon dioxide was charged into the autoclave through a carbon dioxide supply line with pressure regulation function to bring the pressure in the autoclave to 5 MPa. A temperature of the autoclave was controlled to be 70° C. and the polymerization reaction was carried out for 5 h. After the polymerization reaction was complete, the autoclave was cooled to 25° C., the carbon dioxide in the autoclave was discharged, and the unreacted furfuryl glycidyl ether was evacuated in a vacuum drying box at 25° C. to obtain polycarbonate.

In the invention, the prepared polycarbonate was weighed, and the weight of the polycarbonate was 2.85 g. The catalytic system of the metalporphyrin complex prepared according to Example 3 has a TOF of 1340 $h^{-1}$ calculated based on the weight of the polycarbonate. The prepared polycarbonate has a number average molecular weight of 85000 and a molecular weight distribution of 1.15 measured with GPC. It was also subjected to a $^1$H-NMR analysis, and the analytic results show that in the prepared polycarbonate, the cyclic carbonate byproduct is less than 5%, and the carbonate unit content is higher than 99%.

Example 11

The autoclave was subjected to water removal and oxygen removal treatment according to the technical solution described in Example 8.

In a glovebox, 0.03 mmol of the metalporphyrin complex prepared according to Example 4 and 75 mmol of dry epoxychloropropane were added to a 15 mL autoclave that had been subjected to water removal and oxygen removal treatment. Then the autoclave was taken out of the glovebox and carbon dioxide was charged into the autoclave through a carbon dioxide supply line with pressure regulation function to bring the pressure in the autoclave to 4 MPa. A temperature of the autoclave was controlled to be 0° C. and the polymerization reaction was carried out for 48 h. After the polymerization reaction was complete, the autoclave was cooled to 25° C., the carbon dioxide in the autoclave was discharged, and the unreacted epoxychloropropane was evacuated in a vacuum drying box at 25° C. to obtain a polycarbonate.

In the invention, the prepared polycarbonate was weighed, and the weight of the polycarbonate was 2.35 g. The catalytic system of the metalporphyrin complex prepared according to Example 4 has a TOF of 167 $h^{-1}$ calculated based on the weight of the polycarbonate. The prepared polycarbonate has a number average molecular weight of 42000 and a molecular weight distribution of 1.11 measured with GPC. It was also subjected to a $^1$H-NMR analysis, and the analytic results show that in the prepared polycarbonate, the cyclic carbonate byproduct is less than 10%, and the carbonate unit content is higher than 99%.

Example 12

The autoclave was subjected to water removal and oxygen removal treatment according to the technical solution described in Example 8.

In a glovebox, 0.00075 mmol of the metalporphyrin complex prepared according to Example 5 and 75 mmol of dry propylene oxide were added to a 15 autoclave that had been subjected to water removal and oxygen removal treatment. Then the autoclave was taken out of the glovebox and carbon dioxide was charged into the autoclave through a carbon dioxide supply line with pressure regulation function to bring the pressure in the autoclave to 4 MPa. A temperature of the autoclave was controlled to be 120° C. and the polymerization reaction was carried out for 2 h. After the polymerization reaction was complete, the autoclave was cooled to 25° C., the carbon dioxide in the autoclave was discharged, and the unreacted propylene oxide was evacuated in a vacuum drying box at 25° C. to obtain a polycarbonate.

In the invention, the prepared polycarbonate was weighed, and the weight of the polycarbonate was 2.86 g. The catalytic system of the metalporphyrin complex prepared according to Example 5 has a TOF of 2670 $h^{-1}$ calculated based on the weight of the polycarbonate. The prepared polycarbonate has a number average molecular weight of 135000 and a molecular weight distribution of 1.12 measured with GPC. It was also subjected to a $^1$H-NMR analysis, and the analytic results show that in the prepared polycarbonate, the cyclic carbonate byproduct is less than 5%, and the carbonate unit content is higher than 99%.

Example 13

The autoclave was subjected to water removal and oxygen removal treatment according to the technical solution described in Example 8.

In a glovebox, 0.015 mmol of the metalporphyrin complex prepared according to Example 6 and 75 mmol of dry epoxychloropropane were added to a 15 mL autoclave that had been subjected to water removal and oxygen removal treatment. Then the autoclave was taken out of the glovebox and carbon dioxide was charged into the autoclave through a carbon dioxide supply line with pressure regulation function to bring the pressure in the autoclave to 5 MPa. A temperature of the autoclave was controlled to be 0° C. and the polymerization reaction was carried out for 5 h. After the polymerization reaction was complete, the autoclave was cooled to 25° C., the carbon dioxide in the autoclave was discharged, and the unreacted epoxychloropropane was evacuated in a vacuum drying box at 25° C. to obtain a polycarbonate.

In the invention, the prepared polycarbonate was weighed, and the weight of the polycarbonate was 3.1 g. The catalytic system of the metalporphyrin complex prepared according to Example 6 has a TOE of 302 $h^{-1}$ calculated based on the weight of the polycarbonate. The prepared polycarbonate has a number average molecular weight of 44000 and a molecular weight distribution of 1.13 measured with GPC. It was also subjected to a $^1$H-NMR analysis, and the analytic results show that in the prepared polycarbonate, the cyclic carbonate byproduct is less than 5%, and the carbonate unit content is higher than 99%.

Example 14

The autoclave was subjected to water removal and oxygen removal treatment according to the technical solution described in Example 8.

In a glovebox, 0.015 mmol of the metalporphyrin complex prepared according to Example 7 and 75 mmol of dry propylene oxide were added to a 15 mL autoclave that had been subjected to water removal and oxygen removal treatment. Then the autoclave was taken out of the glovebox and carbon dioxide was charged into the autoclave through a carbon dioxide supply line with pressure regulation function to bring the pressure in the autoclave to 2 MPa. A temperature of the autoclave was controlled to be 120° C. and the polymerization reaction was carried out for 0.5 h. After the polymerization reaction was complete, the autoclave was cooled to 25° C., the carbon dioxide in the autoclave was discharged, and the unreacted propylene oxide was evacuated in a vacuum drying box at 25° C. to obtain polycarbonate.

In the invention, the prepared polycarbonate was weighed, and the weight of the polycarbonate was 2.95 g. The catalytic system of the metalporphyrin complex prepared according to Example 7 has a TOF of 4610 $h^{-1}$ calculated based on the weight of the polycarbonate. The prepared polycarbonate has a number average molecular weight of 90000 and a molecular weight distribution of 1.13 measured with GPC. It was also subjected to a $^1$H-NMR analysis, and the analytic results show that in the prepared polycarbonate, the cyclic carbonate byproduct is less than 5%, and the carbonate unit content is higher than 99%.

Example 15

The autoclave was subjected to water removal and oxygen removal treatment according to the technical solution described in Example 8.

In a glovebox, 0.015 mmol of the metalporphyrin complex prepared according to Example 6 and 75 mmol of dry styrene oxide were added to a 15 mL autoclave that had been subjected to water removal and oxygen removal treatment. Then the autoclave was taken out of the glovebox and carbon dioxide was charged into the autoclave through a carbon dioxide supply line with pressure regulation function to bring the pressure in the autoclave to 2 MPa. A temperature of the autoclave was controlled to be 70° C. and the polymerization reaction was carried out for 5 h. After the polymerization reaction was complete, the autoclave was cooled to 25° C., the carbon dioxide in the autoclave was discharged, and the unreacted styrene oxide was evacuated in a vacuum drying box at 25° C. to obtain a polycarbonate.

In the invention, the prepared polycarbonate was weighed, and the weight of the polycarbonate was 3.32 g. The catalytic system of the metalporphyrin complex prepared according to Example 6 has a TOF of 420 $h^{-1}$ calculated based on the weight of the polycarbonate. The prepared polycarbonate has a number average molecular weight of 75000 and a molecular weight distribution of 1.14 measured with GPC. It was also subjected to a $^1$H-NMR analysis, and the analytic results show that in the prepared polycarbonate, the cyclic carbonate byproduct is less than 5%, and the carbonate unit content is higher than 99%.

Example 16

The autoclave was subjected to water removal and oxygen removal treatment according to the technical solution described in Example 8.

In a glovebox, 0.005 mmol of the metalporphyrin complex prepared according to Example 5 and 75 mmol of dry propylene oxide were added to a 15 mL autoclave that had been subjected to water removal and oxygen removal treatment. Then the autoclave was taken out of the glovebox and carbon dioxide was charged into the autoclave through a carbon dioxide supply line with pressure regulation function to bring the pressure in the autoclave to 3 MPa. A temperature of the autoclave was controlled to be 90° C. and the polymerization reaction was carried out for 0.5 h. After the polymerization reaction was complete, the autoclave was cooled to 25° C., the carbon dioxide in the autoclave was discharged, and the unreacted propylene oxide was evacuated in a vacuum drying box at 25° C. to obtain a polycarbonate.

In the invention, the prepared polycarbonate was weighed, and the weight of the polycarbonate was 1.95 g. The catalytic system of the metalporphyrin complex prepared according to Example 5 has a TOF of 3620 $h^{-1}$ calculated based on the weight of the polycarbonate. The prepared polycarbonate has a number average molecular weight of 50000 and a molecular weight distribution of 1.15 measured with GPC. It was also subjected to a $^1$H-NMR analysis, and the analytic results show that in the prepared polycarbonate, the cyclic carbonate byproduct is less than 5%, and the carbonate unit content is higher than 99%.

Example 17

The autoclave was subjected to water removal and oxygen removal treatment according to the technical solution described in Example 8.

In a glovebox, 0.015 mmol of the metalporphyrin complex prepared according to Example 4 and 75 mmol of dry propylene oxide were added to a 15 mL autoclave that had been subjected to water removal and oxygen removal treatment. Then the autoclave was taken out of the glovebox and carbon dioxide was charged into the autoclave through a carbon dioxide supply line with pressure regulation function to bring the pressure in the autoclave to 2 MPa. A temperature of the autoclave was controlled to be 90° C. and the polymerization reaction was carried out for 5 h. After the polymerization reaction was complete, the autoclave was cooled to 25° C., the carbon dioxide in the autoclave was discharged, and the unreacted propylene oxide was evacuated in a vacuum drying box at 25° C. to obtain a polycarbonate.

In the invention, the prepared polycarbonate was weighed, and the weight of the polycarbonate was 2.61 g. The catalytic system of the metalporphyrin complex prepared according to Example 4 has a TOE of 408 $h^{-1}$ calculated based on the weight of the polycarbonate. The prepared polycarbonate has a number average molecular weight of 38000 and a molecular weight distribution of 1.15 measured with GPC. It was also subjected to a $^1$H-NMR analysis, and the analytic results show that in the prepared polycarbonate, the cyclic carbonate byproduct is less than 5%, and the carbonate unit content is higher than 99%.

Example 18

The autoclave was subjected to water removal and oxygen removal treatment according to the technical solution described in Example 8.

In a glovebox, 0.015 mmol of the metalporphyrin complex prepared according to Example 3 and 75 mmol of dry propylene oxide were added to a 15 mL autoclave that had been subjected to water removal and oxygen removal treatment. Then the autoclave was taken out of the glovebox and carbon dioxide was charged into the autoclave through a carbon dioxide supply line with pressure regulation function to bring the pressure in the autoclave to 5 MPa. A temperature of the autoclave was controlled to be 70° C. and the polymerization reaction was carried out for 5 h. After the polymerization reaction was complete, the autoclave was cooled to 25° C., the carbon dioxide in the autoclave was discharged, and the unreacted propylene oxide was evacuated in a vacuum drying box at 25° C. to obtain a polycarbonate.

In the invention, the prepared polycarbonate was weighed, and the weight of the polycarbonate was 2.85 g. The catalytic system of the metalporphyrin complex prepared according to Example 3 has a TOF of 446 $h^{-1}$ calculated based on the weight of the polycarbonate. The prepared polycarbonate has a number average molecular weight of 62000 and a molecular weight distribution of 1.16 measured with GPC. It was also subjected to a $^1$H-NMR analysis, and the analytic results show that in the prepared polycarbonate, the cyclic carbonate byproduct is less than 5%, and the carbonate unit content is higher than 99%.

Example 19

The autoclave was subjected to water removal and oxygen removal treatment according to the technical solution described in Example 8.

In a glovebox, 0.015 mmol of the metalporphyrin complex prepared according to Example 1 and 75 mmol of dry propylene oxide were added to a 15 mL autoclave that had been subjected to water removal and oxygen removal treatment. Then the autoclave was taken out of the glovebox and carbon dioxide was charged into the autoclave through a carbon dioxide supply line with pressure regulation function to bring the pressure in the autoclave to 2 MPa. A temperature of the autoclave was controlled to be 70° C. and the polymerization reaction was carried out for 5 h. After the polymerization reaction was complete, the autoclave was cooled to 25° C., the carbon dioxide in the autoclave was discharged, and the unreacted propylene oxide was evacuated in a vacuum drying box at 25° C. to obtain a polycarbonate.

In the invention, the prepared polycarbonate was weighed, and the weight of the polycarbonate was 2.8 g. The catalytic system of the metalporphyrin complex prepared according to Example 1 has a TOF of 438 $h^{-1}$ calculated based on the weight of the polycarbonate. The prepared polycarbonate has a number average molecular weight of 50000 and a molecular weight distribution of 1.15 measured with GPC. It was also subjected to a $^1$H-NMR analysis, and the analytic results show that in the prepared polycarbonate, the cyclic carbonate byproduct is less than 5%, and the carbonate unit content is higher than 99%.

Comparative Example 1

The autoclave was subjected to water removal and oxygen removal treatment according to the technical solution described in Example 8.

In a glovebox, 0.025 mmol tetraphenylporphyrin aluminum chloride-tetrabutyl ammonium bromide (TPPAlCl-TBAB) and 75 mmol of dry propylene oxide were added to a 15 mL autoclave that had been subjected to water removal and oxygen removal treatment. Then the autoclave was taken out of the glovebox and carbon dioxide was charged into the autoclave through a carbon dioxide supply line with pressure regulation function to bring the pressure in the autoclave to 4 MPa. A temperature of the autoclave was controlled to be 25° C. and the polymerization reaction was carried out for 5 h. After the polymerization reaction was complete, the autoclave was cooled to 25° C., the carbon dioxide in the autoclave was discharged, and the unreacted propylene oxide was evacuated in a vacuum drying box at 25° C. to obtain a polycarbonate.

In the invention, the prepared polycarbonate was weighed, and the weight of the polycarbonate was 0.09 g. The TPPAlCl-TBAB catalytic system has a TOF of 2.3 $h^{-1}$ calculated based on the weight of the polycarbonate. The prepared polycarbonate has a number average molecular weight of 8900 and a molecular weight distribution of 1.15 measured with GPC. It was also subjected to a $^1$H-NMR analysis, and the analytic results show that in the prepared polycarbonate, the cyclic carbonate byproduct is about 30%, and the carbonate unit content is about 95%.

Comparative Example 2

The autoclave was subjected to water removal and oxygen removal treatment according to the technical solution described in Example 8.

In a glovebox, 0.015 mmol tetraphenylporphyrin aluminum chloride-bis(triphenylphosphine) ammonium chloride (TPPAlCl-PPNCl) and 75 mmol of dry propylene oxide were added to a 15 mL autoclave that had been subjected to water removal and oxygen removal treatment. Then the autoclave was taken out of the glovebox and carbon dioxide was charged into the autoclave through a carbon dioxide supply line with pressure regulation function to bring the pressure in the autoclave to 2 MPa. A temperature of the autoclave was controlled to be 90° C. and the polymerization reaction was carried out for 5 h. After the polymerization reaction was complete, the autoclave was cooled to 25° C., the carbon dioxide in the autoclave was discharged, and the unreacted propylene oxide was evacuated in a vacuum drying box at 25° C.

In the invention, the reaction product prepared in Comparative Example 2 was determined, but production of polymer was not detected and the TPPAlCl-PPNCl catalytic system lost its activity. Therefore, the metalporphyrin complex provided according to the invention is more stable than the metalporphyrin complex provided in the prior art and maintains a higher catalytic activity at high temperatures.

As can be seen from the above examples, the invention provides a metalporphyrin complex having a structure represented by formula (I), wherein $R_1$, $R_2$, $R_3$, $R_4$, $R_5$, $R_6$, $R_7$, $R_8$, $R_9$ and $R_{10}$ are independently one selected from the group consisting of hydrogen, halogen, an aliphatic group, a substituted heteroaliphatic group, an aryl group and a substituted heteroaryl group; n is a degree of polymerization and ranges from 1 to 6; L is one of a quaternary ammonium functional group and a quaternary phosphonium functional group; M is a metal element; and X is one selected from the group consisting of halogen, —$NO_3$, $CH_3COO$—, $CCl_3COO$—, $CF_3COO$—, $ClO_4$—, $BF_4$—, $BPh_4$-, —$N_3$, p-methyl benzoate, p-methyl benzenesulfonate, o-nitrophenolate anion, p-nitrophenolate anion, m-nitrophenolate anion, 2,4-dinitrophenolate anion, 3,5-dinitrophenolate anion, 2,4,6-trinitrophenolate anion, 3,5-dichlorophenolate anion, 3,5-difluorophenolate anion, 3,5-bis(trifluoromethyl) phenolate anion and pentafluorophenolate anion. In the invention, the metalporphyrin complex contains two quaternary ammonium functional groups or two quaternary phosphonium functional groups, and possesses higher catalytic activity compared with those of the prior art when catalyzing the polymerization reaction of carbon dioxide and an epoxy compound. Further, in catalyzing the polymerization reaction of carbon dioxide and the epoxy compound, the metalporphyrin complex provided according to the invention has higher product selectivity, produces less cyclic carbonate byproducts, and results in the obtained polycarbonate having a higher number average molecular weight.

The description of the above examples is provided to aid in understanding the methods and core concepts of the invention only. It should be noted that for those of ordinary skill in the art, several improvements and modifications can be made to the invention without departing from the principles of the invention, and those improvements and modifications also fall within the scope defined by the claims of the invention. The various modifications to these examples are apparent to those skilled in the art, and the general principles defined herein may be embodied in other examples without departing from the spirit or scope of the invention. Therefore, the invention is not limited to these examples illustrated herein, but corresponds to the widest scope in consistent with the principles and novel features disclosed herein.

The invention claimed is:

1. A metalporphyrin complex, having a structure represented by Formula (I):

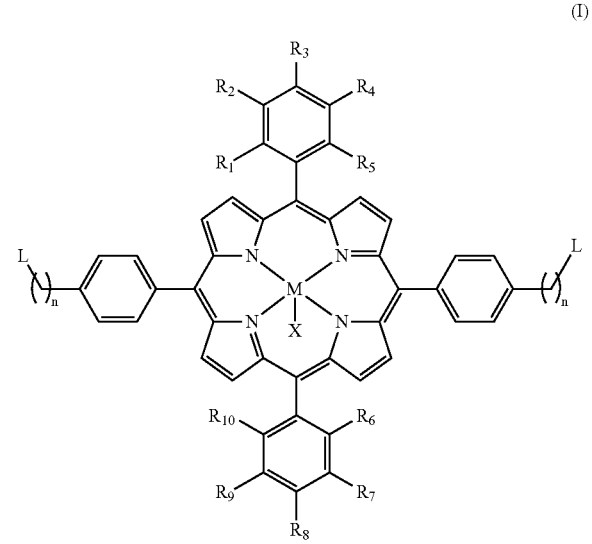

wherein $R_1$, $R_2$, $R_4$, $R_5$, $R_6$, $R_7$, $R_8$, $R_9$ and $R_{10}$ are independently one selected from the group consisting of hydrogen, halogen, an aliphatic group having a number of carbon atoms from 1 to 5, a substituted heteroaliphatic group having a number of carbon atoms from 1 to 5 with oxygen as the heteroatom, and a halogen-substituted heteroaryl group having a number of benzene rings from 1 to 3;

n is a degree of polymerization and ranges from 1 to 6;

L is one of a quaternary ammonium functional group and a quaternary phosphonium functional group;

M is Al; and

X is one selected from the group consisting of halogen, —$NO_3$, $CH_3COO$—, $CCl_3COO$—, $CF_3COO$—, $ClO_4$—, $BF_4$—, $BPh_4$-, —CN, —$N_3$, p-methyl benzoate, p-methyl benzenesulfonate, o-nitrophenolate anion, p-nitrophenolate anion, m-nitrophenolate anion, 2,4-dinitrophenolate anion, 3,5-dinitrophenolate anion, 2,4,6-trinitrophenolate anion, 3,5-dichlorophenolate anion, 3,5-difluorophenolate anion, 3,5-bis(trifluoromethyl)phenolate anion and pentafluorophenolate anion.

2. The metalporphyrin complex according to claim 1, wherein L in Formula (I) is one of a quaternary ammonium functional group having a structure represented by Formula (II) and a quaternary phosphonium functional group having a structure represented by Formula (III),

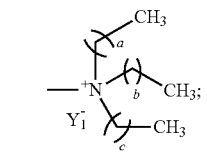
(II)

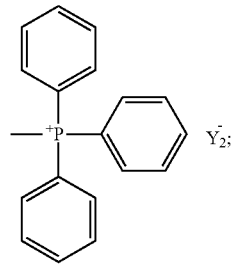
(III)

in Formula (II), a, b and c are degrees of polymerization and independently range from 1 to 6;

$Y_1^-$ in Formula (II) and $Y_2^-$ in Formula (III) are independently one selected from the group consisting of halogen anion, $NO_3^-$, $CH_3COO^-$, $CCl_3COO^-$, $CF_3COO^-$, $ClO_4^-$, $BF_4^-$, p-methyl benzoate, p-methyl benzenesulfonate, o-nitrophenolate anion, p-nitrophenolate anion, m-nitrophenolate anion, 2,4-dinitrophenolate anion, 3,5-dinitrophenolate anion, 2,4,6-trinitrophenolate anion, 3,5-dichlorophenolate anion, 3,5-difluorophenolate anion, 3,5-bis(trifluoromethyl)phenolate anion and pentafluorophenolate anion.

3. The metalporphyrin complex according to claim 2, wherein $Y_1^-$ in Formula (II) and $Y_2^-$ in Formula (III) are independently one selected from the group consisting of halogen anion, $NO_3^-$, $CH_3COO^-$, $BF_4^-$, p-methyl benzoate, o-nitrophenolate anion, 2,4-dinitrophenolate anion, 2,4,6-trinitrophenolate anion, 3,5-dichlorophenolate anion and pentafluorophenolate anion.

4. The metalporphyrin complex according to claim 1, wherein the M is one of iron element and aluminum element.

5. The metalporphyrin complex according to claim 1, wherein the X is one selected from the group consisting of halogen, —$NO_3$, $CH_3COO$—, $BF_4$—, p-methyl benzoate, o-nitrophenolate anion, 2,4-dinitrophenolate anion, 2,4,6-trinitrophenolate anion, 3,5-dichlorophenolate anion and pentafluorophenolate anion.

6. A method for preparing a metalporphyrin complex according to claim 1, comprising the steps of:
step a), in which under an action of a catalyst, a first reaction between a first compound having a structure represented by Formula (1) and dichlorodimethyl methyl ether occurs in a solvent to obtain a second compound having a structure represented by Formula (2); and in the Formula (1), n ranges from 1 to 6, and Y is an anion in a quaternary ammonium functional group or the anion in a quaternary phosphonium functional group;

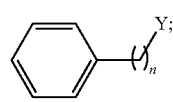
(1)

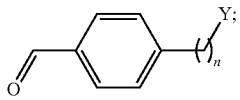
(2)

step b), in which a second reaction between a third compound having a structure represented by Formula (3) and pyrrole occurs under an action of indium chloride, and the resultant product from the second reaction and sodium hydroxide are subjected to a third reaction to obtain a fourth compound having a structure represented by Formula (4);

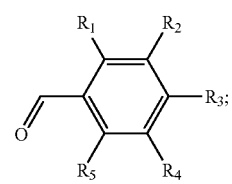
(3)

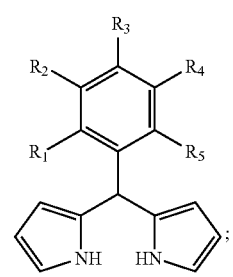
(4)

step c), in which a fourth reaction between a fifth compound having a structure represented by Formula (5) and pyrrole occurs under an action of indium chloride, and the resultant product from the fourth reaction and sodium hydroxide are subjected to a fifth reaction to obtain a sixth compound having a structure represented by Formula (6);

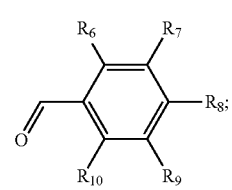
(5)

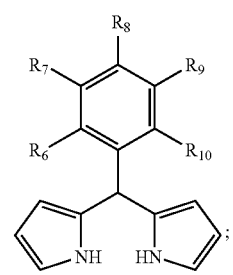
(6)

step d), in which under an action of a catalyst, the second compound obtained in the step a), the fourth compound obtained in the step b) and the sixth compound obtained in the step c) are subjected to a sixth reaction in a solvent, and the resultant product from the sixth reaction and 2,3-dichloro-5,6-dicyano-1,4-benzoquinone are subjected to a seventh reaction to obtain a seventh compound having a structure represented by Formula (7);

(7)

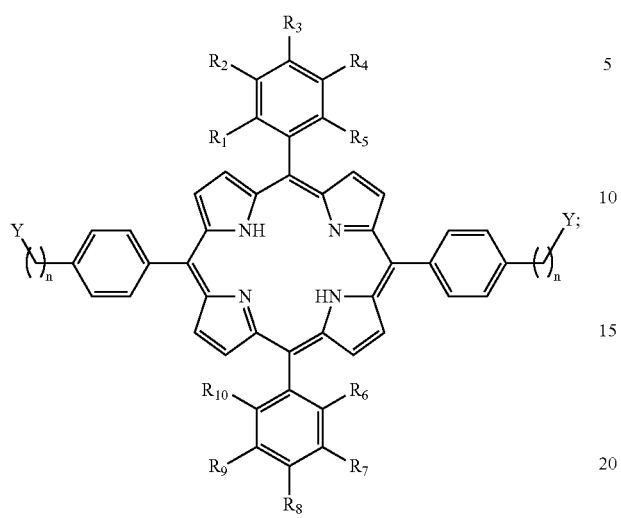

step e), in which an eighth reaction between the seventh compound obtained in the step d) and a metal salt compound occurs in a solvent to obtain an eighth compound having a structure represented by Formula (8); and in the Formula (8), M is Al, and X is one selected from the group consisting of halogen, $-NO_3$, $CH_3COO-$, $CCl_3COO-$, $CF_3COO-$, $ClO_4-$, $BF_4-$, $BPh_4-$, $-CN$, $-N_3$, p-methyl benzoate, p-methyl benzenesulfonate, o-nitrophenolate anion, p-nitrophenolate anion, m-nitrophenolate anion, 2,4-dinitrophenolate anion, 3,5-dinitrophenolate anion, 2,4,6-trinitrophenolate anion, 3,5-dichlorophenolate anion, 3,5-difluorophenolate anion, 3,5-bis(trifluoromethyl) phenolate anion and pentafluorophenolate anion;

(8)

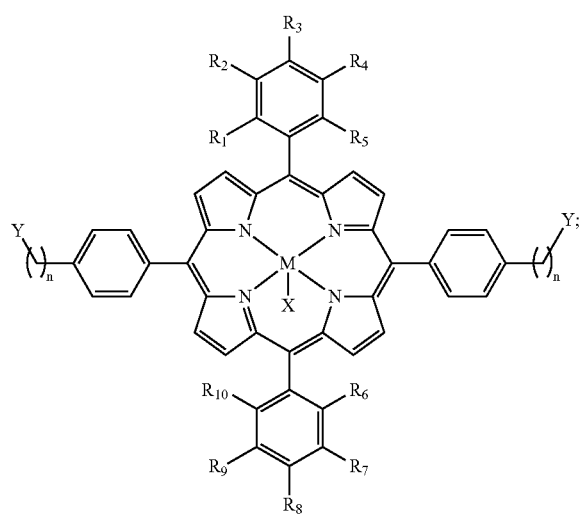

and step f), in which a ninth reaction between the eighth compound obtained in the step e) and a tertiary amine compound occurs in a solvent, or a tenth reaction between the eighth compound obtained in the step e) and a tertiary phosphine compound occurs in a solvent, to obtain the metalporphyrin complex having the structure represented by Formula (I); and L in the Formula (I) is one of a quaternary ammonium functional group and a quaternary phosphonium functional group;

(I)

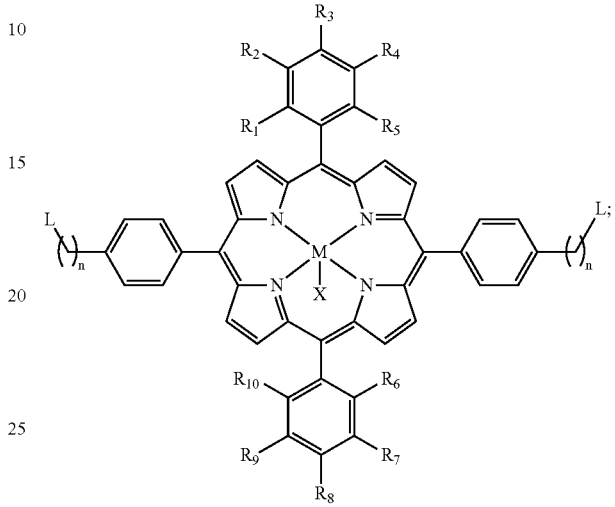

and the temporal sequence of the step a), step b) and step c) are not limited;

wherein R1, R2, R4, R5, R6, R7, R9 and R10 are independently one selected from the group consisting of hydrogen, halogen, an aliphatic group having a number of carbon atoms from 1 to 5, a substituted heteroaliphatic group having a number of carbon atoms from 1 to 5 with oxygen as the heteroatom, and a halogen-substituted heteroaryl group having a number of benzene rings from 1 to 3; and R3 and R8 are independently one selected from the group consisting of halogen, aliphatic group having a number of carbon atoms from 1 to 5, a substituted heteroaliphatic group having a number of carbon atoms from 1 to 5 with oxygen as the heteroatom, and a halogen-substituted heteroaryl group having a number of benzene rings from 1 to 3.

7. The method according to claim 6, wherein a mass ratio of the catalyst, the first compound, dichlorodimethyl methyl ether and the solvent in the step a) is (1-5):(1-3):1:(15-25);

a mass ratio of the third compound, pyrrole, indium chloride and sodium hydroxide in the step b) is (4-7):(240-260):1:(15-25);

a mass ratio of the second compound, the fourth compound, the sixth compound, the catalyst, the solvent and 2,3-dichloro-5,6-dicyano-1,4-benzoquinone in the step d) is (0.5-1.5):1:(0.5-2):(2-4):(1200-1800):(1-3); and a mass ratio of the eighth compound, the tertiary amine compound and the solvent in the step f) is 1:(30-45):(120-160).

8. The method according to claim 6, wherein the Y is one selected from the group consisting of halogen anion, $NO_3^-$, $CH_3COO^-$, $CCl_3COO^-$, $CF_3COO^-$, $ClO_4^-$, $BF_4^-$, p-methyl benzoate, p-methyl benzenesulfonate, o-nitrophenolate anion, p-nitrophenolate anion, m-nitrophenolate anion, 2,4-dinitrophenolate anion, 3,5-dinitrophenolate anion, 2,4,6-trinitrophenolate anion, 3,5-dichlorophenolate anion, 3,5- difluorophenolate anion, 3,5-bis(trifluoromethyl)phenolate anion and pentafluorophenolate anion;

the third compound or fifth compound is one selected from the group consisting of benzaldehyde, pentafluorobenzaldehyde, p-methyl benzaldehyde, p-ethoxy benzaldehyde, p-phenyl benzaldehyde and 3-chlurobiphenyl-4-benzaldehyde;

the tertiary amine compound is one selected from the group consisting of trimethylamine, tributylamine and trihexylamine; and the tertiary phosphine compound is triphenylphosphine.

9. The method according to claim 6, wherein the first reaction is carried out at a temperature of 25 to 45° C. for 20 to 40 min;

the second reaction is carried out at a temperature of 20 to 40° C. for 1 to 3 h;

the third reaction is carried out at a temperature of 20 to 40° C. for 30 to 60 min;

the sixth reaction is carried out at a temperature of 20 to 40° C. for 0.5 to 1.5 h; and the seventh reaction is carried out at a temperature of 20 to 40° C. for 0.5 to 1.5 h.

10. A method for preparing a polycarbonate, comprising the steps of:

subjecting carbon dioxide and an epoxy compound to a polymerization reaction under an action of a catalyst to obtain the polycarbonate;

wherein the catalyst is the metalporphyrin complex according to claim 1.

11. The method according to claim 10, wherein a molar ratio of the catalyst to the epoxy compound is 1:(2500-100000);

wherein a pressure of the polymerization reaction is 0.1 to 5 MPa.

12. The method according to claim 10, wherein the polymerization reaction is carried out at 0 to 120° C. for 0.5 to 48 h.

* * * * *